United States Patent
Numata

(10) Patent No.: US 11,233,200 B2
(45) Date of Patent: Jan. 25, 2022

(54) CONDENSED CYCLIC COMPOUND, COMPOSITION INCLUDING THE SAME, AND ORGANIC LIGHT-EMITTING DEVICE INCLUDING THE CONDENSED CYCLIC COMPOUND

(71) Applicant: Samsung Electronics Co., Ltd., Suwon-si (KR)

(72) Inventor: Masaki Numata, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 364 days.

(21) Appl. No.: 16/236,953

(22) Filed: Dec. 31, 2018

(65) Prior Publication Data

US 2019/0221746 A1 Jul. 18, 2019

(30) Foreign Application Priority Data

Jan. 16, 2018 (JP) .............................. JP2018-005081
Jun. 29, 2018 (KR) ........................ 10-2018-0075657

(51) Int. Cl.
| | | |
|---|---|---|
| H01L 51/00 | (2006.01) | |
| C07C 13/72 | (2006.01) | |
| C09K 11/06 | (2006.01) | |
| C07D 209/86 | (2006.01) | |
| C07D 239/26 | (2006.01) | |
| C07D 241/12 | (2006.01) | |
| C07D 213/06 | (2006.01) | |
| C07D 307/91 | (2006.01) | |
| C07D 333/76 | (2006.01) | |
| H01L 51/50 | (2006.01) | |

(52) U.S. Cl.
CPC .......... *H01L 51/0056* (2013.01); *C07C 13/72* (2013.01); *C07D 209/86* (2013.01); *C07D 213/06* (2013.01); *C07D 239/26* (2013.01); *C07D 241/12* (2013.01); *C07D 307/91* (2013.01); *C07D 333/76* (2013.01); *C09K 11/06* (2013.01); *C07C 2603/04* (2017.05); *C07C 2603/97* (2017.05); *C09K 2211/1007* (2013.01); *C09K 2211/1011* (2013.01); *H01L 51/5004* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 2251/552* (2013.01)

(58) Field of Classification Search
None
See application file for complete search history.

(56) References Cited

U.S. PATENT DOCUMENTS

| | | |
|---|---|---|
| 8,859,111 B2 | 10/2014 | Parham et al. |
| 2007/0262703 A1 | 11/2007 | Tsai et al. |
| 2012/0126179 A1* | 5/2012 | Parham ............... C07D 209/86 252/500 |
| 2016/0190477 A1 | 6/2016 | Kawakami et al. |
| 2017/0174705 A1 | 6/2017 | Kato et al. |
| 2017/0179395 A1 | 6/2017 | Kim et al. |
| 2017/0222157 A1 | 8/2017 | Jatsch et al. |
| 2017/0317295 A1 | 11/2017 | No et al. |

FOREIGN PATENT DOCUMENTS

| | | |
|---|---|---|
| EP | 3239136 A2 | 12/2015 |
| EP | 3239136 A2 | 11/2017 |
| JP | 2009-203176 A | 9/2009 |
| JP | 2012-532902 A | 12/2012 |
| JP | 2017114858 A | 6/2017 |
| JP | 2017524699 A | 8/2017 |
| KR | 10-1802348 B1 | 11/2017 |
| KR | 10-1812216 B1 | 12/2017 |
| WO | WO-2011/006574 A1 * | 1/2011 |
| WO | 2015020217 A1 | 2/2015 |
| WO | WO2018006679 A1 | 1/2018 |

OTHER PUBLICATIONS

English Translation of Office Action issued in JP Patent Application No. 2018-005081, dated Sep. 21, 2021, 5 pp.
Office Action issued in JP Patent Application No. 2018-005081, dated Sep. 21, 2021, 4 pp.

* cited by examiner

*Primary Examiner* — Jay Yang
(74) *Attorney, Agent, or Firm* — Cantor Colburn LLP

(57) ABSTRACT

A condensed cyclic compound represented by Formula 1:

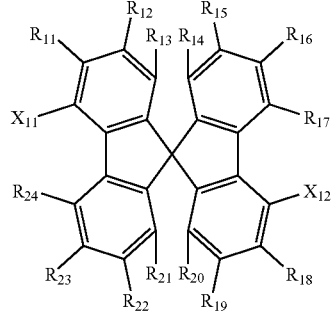

Formula 1 wherein, in Formula 1, $X_{11}$, $X_{12}$, and $R_{11}$ to $R_{24}$ are the same as described in the specification.

19 Claims, 1 Drawing Sheet

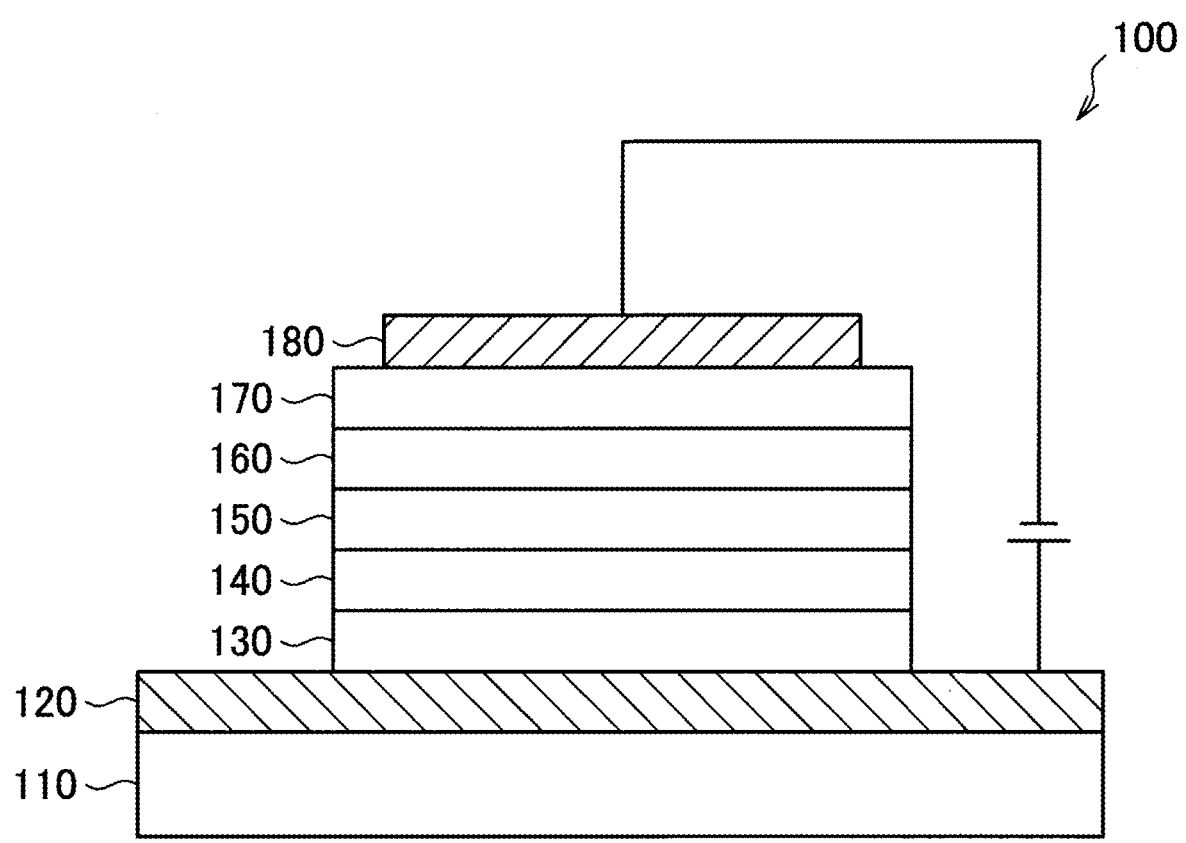

CONDENSED CYCLIC COMPOUND, COMPOSITION INCLUDING THE SAME, AND ORGANIC LIGHT-EMITTING DEVICE INCLUDING THE CONDENSED CYCLIC COMPOUND

CROSS-REFERENCE TO RELATED APPLICATIONS

This application claims priority to Japanese Patent Application No. 2018-005081, filed on Jan. 16, 2018, in the Japanese Patent Office, and Korean Patent Application No. 10-2018-0075657, filed on Jun. 29, 2018, in the Korean Intellectual Property Office, and all the benefits accruing therefrom under 35 U.S.C. 119, the contents of which are incorporated herein in their entireties by reference.

BACKGROUND

1. Field

One or more embodiments relate to a condensed cyclic compound, a composition including the same, and an organic light-emitting device including the condensed cyclic compound.

2. Description of the Related Art

Organic light-emitting devices (OLEDs) are self-emission devices that have wide viewing angles, high contrast ratios, short response times, as well as excellent characteristics in terms of brightness, driving voltage, and response speed, and that produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a condensed cyclic compound, a composition including the condensed cyclic compound, and an organic light-emitting device including the condensed cyclic compound.

The organic light-emitting device including the condensed cyclic compound may provide high current efficiency and a long lifespan. In addition, the condensed cyclic compound may provide characteristics suitable for use in solution process.

Additional aspects will be set forth in part in the description which follows and, in part, will be apparent from the description, or may be learned by practice of the presented embodiments.

An aspect provides a condensed cyclic compound represented by Formula 1:

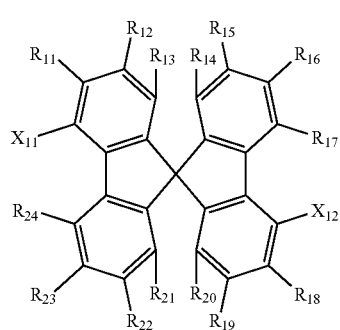

Formula 1

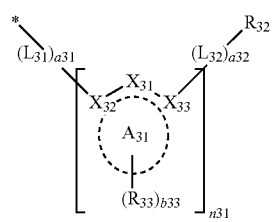

Formula 3

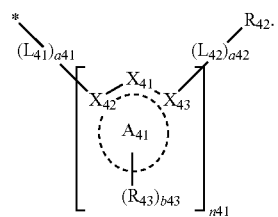

Formula 4

In Formulae 1, 3, and 4, $X_{11}$ may be a group represented by Formula 3, and $X_{12}$ may be a group represented by Formula 4, $X_{31}$ may be selected from N and $C(R_{31})$, and $X_{41}$ may be selected from N and $C(R_{41})$, $X_{32}$, $X_{33}$, $X_{42}$, and $X_{43}$ may each be C, $A_{31}$ and $A_{42}$ may each independently be selected from a $C_6$-$C_{30}$ arene group and a $C_1$-$C_{30}$ heteroarene group, n31 and n41 may each independently be selected from 1, 2, 3, 4, 5, 6, 7, 8, 9, and 10, $L_{31}$, $L_{32}$, $L_{41}$, and $L_{42}$ may each independently be selected from a single bond, a substituted or unsubstituted $C_5$-$C_{30}$ carbocyclic group, and a substituted or unsubstituted $C_1$-$C_{30}$ heterocyclic group, a31, a32, a41, and a42 may each independently be selected from 0, 1, 2, and 3, $R_{32}$ and $R_{42}$ may each independently be selected from a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group, $R_{11}$ to $R_{24}$, $R_{31}$, $R_{33}$, $R_{41}$, and $R_{43}$ may each independently be selected from hydrogen, deuterium, —F, —Cl, —Br, —I, a cyano group, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_7$-$C_{30}$ alkylaryl group, a substituted or unsubstituted $C_6$-$C_{30}$ aryloxy group, a substituted or unsubstituted $C_6$-$C_{30}$ arylthio group, a substituted or unsubstituted $C_1$-$C_{30}$ heteroaryl group, a substituted or unsubstituted $C_2$-$C_{30}$ alkylheteroaryl group, a substituted or unsubstituted $C_1$-$C_{30}$ heteroaryloxy group, a substituted or unsubstituted $C_1$-$C_{30}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —N($Q_1$)($Q_2$), b33 and b43 may each independently be selected from 1, 2, 3, 4, 5, 6, 7, 8, 9, and 10, $Q_1$ to $Q_3$ may each independently be selected from hydrogen, deuterium, a $C_1$-$C_{30}$ alkyl group, a $C_1$-$C_{30}$ alkoxy group, a $C_6$-$C_{30}$ aryl group, a $C_1$-$C_{30}$ heteroaryl group, a monovalent non-aromatic condensed polycyclic group, a monovalent non-aromatic condensed heteropolycyclic group, a $C_1$-$C_{30}$ alkyl group substituted with at least one selected from deuterium, —F, a cyano group, a $C_1$-$C_{30}$ alkyl group, and a $C_6$-$C_{30}$ aryl group, and a $C_6$-$C_{30}$ aryl group substituted with at least one selected from deuterium, —F, a cyano group, a $C_1$-$C_{30}$ alkyl group, and a $C_6$-$C_{30}$ aryl group, and

* indicates a binding site to a neighboring atom.

Another aspect provides a composition including at least one of the condensed cyclic compound represented by Formula 1.

Another aspect provides an organic light-emitting device including:
a first electrode;
a second electrode; and
an organic layer disposed between the first electrode and the second electrode,
wherein the organic layer includes an emission layer, and
wherein the organic layer includes at least one condensed cyclic compound.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section.

Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Condensed Cyclic Compound

A condensed cyclic compound represented by Formula 1 according to an embodiment will be described:

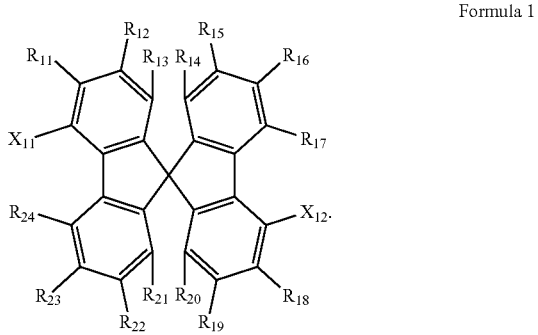

Formula 1

In Formula 1, $X_{11}$ may be a group represented by Formula 3, and $X_{12}$ may be a group represented by Formula 4:

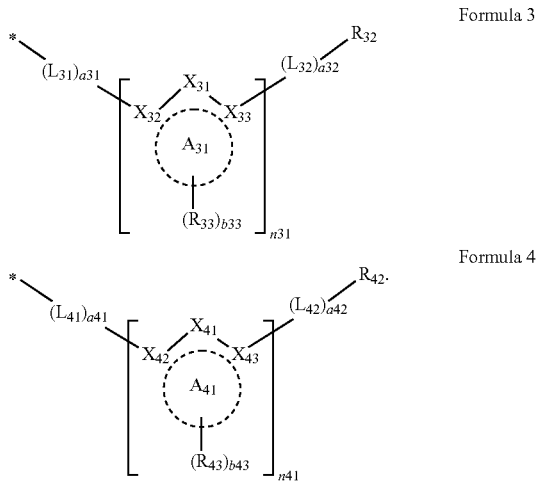

Formula 3

Formula 4

In Formulae 3 and 4, * indicates a binding site to a neighboring atom, and $X_{31}$ to $X_{33}$, $L_{31}$, $L_{32}$, a31, a32, $R_{32}$, $R_{33}$, b33, n31, $X_{41}$ to $X_{43}$, $L_{41}$, $L_{42}$, a41, a42, $R_{42}$, $R_{43}$, b43, and n43 may each independently be the same as described herein.

In Formula 3, $X_{31}$ may be selected from N and $C(R_{31})$.
In Formula 4, $X_{41}$ may be selected from N and $C(R_{41})$.
In Formulae 3 and 4, $X_{32}$, $X_{33}$, $X_{42}$, and $X_{43}$ may each be C.

In Formula 3, i) a bond between $X_{32}$ and $X_{31}$ may be a double bond, and a bond between $X_{31}$ and $X_{33}$ may be a single bond, or ii) a bond between $X_{32}$ and $X_{31}$ may be a single bond, and a bond between $X_{31}$ and $X_{33}$ may be a double bond.

In Formula 4, i) a bond between $X_{42}$ and $X_{41}$ may be a double bond, and a bond between $X_{41}$ and $X_{43}$ may be a single bond, or ii) a bond between $X_{42}$ and $X_{41}$ may be a single bond, and a bond between $X_{41}$ and $X_{43}$ may be a double bond.

In Formulae 3 and 4, $A_{31}$ and $A_{42}$ may each independently be selected from a $C_6$-$C_{30}$ arene group and a $C_1$-$C_{30}$ heteroarene group.

For example, in Formulae 3 and 4, $A_{31}$ and $A_{42}$ may each independently be selected from a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group, but embodiments of the present disclosure are not limited thereto.

In an embodiment, in Formulae 3 and 4, $A_{31}$ and $A_{42}$ may each independently be selected from a benzene group, a pyridine group, a pyridazine group, a pyrimidine group, a pyrazine group, and a triazine group, but embodiments of the present disclosure are not limited thereto.

In Formulae 3 and 4, n31 and n41 may each independently be selected from 1, 2, 3, 4, 5, 6, 7, 8, 9, and 10.

For example, in Formula 3 and 4, n31 and n41 may each independently be selected from 1, 2, and 3, but embodiments of the present disclosure are not limited thereto.

In an embodiment, in Formulae 3 and 4, the sum of n31 and n41 may be selected from 2, 3, 4, 5, and 6, but embodiments of the present disclosure are not limited thereto.

In Formulae 3 and 4, $L_{31}$, $L_{32}$, $L_{41}$, and $L_{42}$ may each independently be selected from a single bond, a substituted or unsubstituted $C_5$-$C_{30}$ carbocyclic group, and a substituted or unsubstituted $C_1$-$C_{30}$ heterocyclic group.

For example, in Formulae 3 and 4, $L_{31}$, $L_{32}$, $L_{41}$, and $L_{42}$ may each independently be selected from:

a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthalene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiophene group, a silole group, a benzofuran group, a benzothiophene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazolinone group, a benzimidazolinone group, an imidazopyridine group, an imidazopyrimidine group, an imidazophenanthridine group, a benzimidazophenanthridine group, an azadibenzofuran group, an azacarbazole group, an azadibenzothiophene group, a diazadibenzofuran group, a diazacarbazole group, a diazadibenzothiophene group, a xanthone group, and a thioxanthone group; and a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthalene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiophene group, a silole group, a benzofuran group, a benzothiophene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazolinone group, a benzimidazolinone group, an imidazopyridine group, an imidazopyrimidine group, an imidazophenanthridine group, a benzimidazophenanthridine group, an azadibenzofuran group, an azacarbazole group, an azadibenzothiophene group, a diazadibenzofuran group, a diazacarbazole group, a diazadibenzothiophene group, a xanthone group, and a thioxanthone group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group, but embodiments of the present disclosure are not limited thereto.

In an embodiment, in Formulae 3 and 4, $L_{31}$, $L_{32}$, $L_{41}$, and $L_{42}$ may each independently be selected from:

a single bond, a benzene group, a naphthalene group, a fluorene group, a carbazole group, a pyridine group, a pyrazine group, a pyridazine group, a pyrimidine group, and a triazine group; and a benzene group, a naphthalene group, a fluorene group, a carbazole group, a pyridine group, a pyrazine group, a pyridazine group, a pyrimidine group, and a triazine group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a naphthyl group, a biphenyl group, and a terphenyl group, but embodiments of the present disclosure are not limited thereto.

In Formulae 3 and 4, a31, a32, a41, and a42 each indicate the number of repetitions of $L_{31}$, $L_{32}$, $L_{41}$, and $L_{42}$, and may each independently be selected from 0, 1, 2, and 3. When a31 is 0, $(L_{31})_{a31}$ may be a single bond.

For example, in Formulae 3 and 4, a31, a32, a41, and a42 may each independently be selected from 0 and 1, but embodiments of the present disclosure are not limited thereto.

In Formulae 3 and 4, $R_{32}$ and $R_{42}$ may each independently be selected from a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group.

For example, in Formulae 3 and 4, $R_{32}$ and $R_{42}$ may each independently be selected from a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group; and a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group, but embodiments of the present disclosure are not limited thereto.

In an embodiment, in Formulae 3 and 4, $R_{32}$ and $R_{42}$ may each independently be selected from:

a phenyl group, a naphthyl group, a fluorenyl group, a phenanthrenyl group, a biphenyl group, a terphenyl group, a triphenylenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, a carbazolyl group, an imidazolyl group, and a benzimidazolyl group; and a phenyl group, a naphthyl group, a fluorenyl group, a phenanthrenyl group, a biphenyl group, a terphenyl group, a triphenylenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, a carbazolyl group, an imidazolyl group, and a benzimidazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a naphthyl group, a biphenyl group, and a terphenyl group, but embodiments of the present disclosure are not limited thereto.

In Formulae 1, 3, and 4, $R_{11}$ to $R_{24}$, $R_{31}$, $R_{33}$, $R_{41}$, and $R_{43}$ may each independently be selected from hydrogen, deuterium, —F, —Cl, —Br, —I, a cyano group, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_7$-$C_{30}$ alkylaryl group, a substituted or unsubstituted $C_6$-$C_{30}$ aryloxy group, a substituted or unsubstituted $C_6$-$C_{30}$ arylthio group, a substituted or unsubstituted $C_1$-$C_{30}$ heteroaryl group, a substituted or unsubstituted $C_2$-$C_{30}$ alkylheteroaryl group, a substituted or unsubstituted $C_1$-$C_{30}$ heteroaryloxy group, a substituted or unsubstituted $C_1$-$C_{30}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —N($Q_1$)($Q_2$), and $Q_1$ to $Q_3$ may each independently be selected from hydrogen, deuterium, a $C_1$-$C_{30}$ alkyl group, a $C_1$-$C_{30}$ alkoxy group, a $C_6$-$C_{30}$ aryl group, a $C_1$-$C_{30}$ heteroaryl group, a monovalent non-aromatic condensed polycyclic group, a monovalent non-aromatic condensed heteropolycyclic group, a $C_1$-$C_{30}$ alkyl group substituted with at least one selected from deuterium, —F, a cyano group, a $C_1$-$C_{30}$ alkyl group, and a $C_6$-$C_{30}$ aryl group, and a $C_6$-$C_{30}$ aryl group substituted with at least one selected from deuterium, —F, a cyano group, a $C_1$-$C_{30}$ alkyl group, and a $C_6$-$C_{30}$ aryl group.

For example, in Formulae 1, 3, and 4, $R_{11}$ to $R_{24}$, $R_{31}$, $R_{33}$, $R_{41}$, and $R_{43}$ may each independently be selected from hydrogen, deuterium, —F, —Cl, —Br, —I, a cyano group, a $C_1$-$C_{30}$ alkyl group, a $C_1$-$C_{30}$ alkoxy group, a $C_6$-$C_{30}$ aryl group, a $C_6$-$C_{30}$ aryloxy group, a $C_1$-$C_{30}$ heteroaryl group, a $C_1$-$C_{30}$ heteroaryloxy group, a monovalent non-aromatic condensed polycyclic group, a substituted or unsubstituted monovalent non-aromatic condensed heteropolycyclic group, and —N($Q_1$)($Q_2$), and $Q_1$ and $Q_2$ may each independently be a $C_1$-$C_{30}$ alkyl group, but embodiments of the present disclosure are not limited thereto.

In an embodiment, in Formulae 1, 3, and 4, $R_{11}$ to $R_{24}$, $R_{31}$, $R_{33}$, $R_{41}$, and $R_{43}$ may each independently be selected from hydrogen, deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, an n-pentyl group, an iso-pentyl group, a tert-pentyl group, a neo-pentyl group, a 1,2-dimethylpropyl group, an n-hexyl group, an iso-hexyl group, a 1,3-dimethylbutyl group, a 1-iso-propylpropyl group, a 1,2-dimethylbutyl group, an n-heptyl group, a 1,4-dimethylpentyl group, a 3-ethylpentyl group, a 2-methyl-1-iso-propylpropyl group, a 1-ethyl-3-methylbutyl group, an n-octyl group, a 2-ethylhexyl group, a 3-methyl-1-iso-propylbutyl group, a 2-methyl-1-iso-propyl group, a 1-tert-butyl-2-methylpropyl group, an n-nonyl group, a 3,5,5-trimethyldecyl group, an n-decyl group, an isodecyl group, n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, an n-tetracosyl group, a methoxy group, an ethoxy group, a propoxy group, an iso-propoxy group, an n-butoxy group, an iso-butoxy group, a sec-butoxy group, a tert-butoxy group, an n-pentoxy group, an iso-pentoxy group, a tert-pentoxy group, a neo-pentoxy group, an n-hexyloxy group, an iso-hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, a 3-ethylpentyloxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, a thioxanthonyl group, a phenoxy group, a 1-naphthyloxy group, a 2-naphthyloxy group, a 2-azulenyloxy group, a 2-furanyloxy group, a 2-thienyloxy group, a 2-indolyloxy group, a 3-indolyloxy group, a 2-benzofuriloxy group, a 2-benzothienyloxy group, an N-methylamino group, an N-ethylamino group, an N-propylamino group, an N-iso-propylamino group, an N-butylamino group, an N-iso-butylamino group, an N-sec-butylamino group, an N-tert-butylamino group, an N-pentylamino group, an N-hexylamino group, an N,N-dimethylamino group, an N,N-diethylamino group, an N,N-dipropylamino group, an N,N-diisoropylamino group, an N,N-dibutylamino group, am N,N-di-iso-butylamino group, an N,N-dipentylamino group, and an N,N-dihexylamino group, but embodiments of the present disclosure are not limited thereto.

In an embodiment, in Formula 1, $R_{11}$ to $R_{24}$ may each independently be hydrogen, but embodiments of the present disclosure are not limited thereto.

In an embodiment, in Formula 1, $R_{31}$ and $R_{41}$ may each independently be hydrogen, but embodiments of the present disclosure are not limited thereto.

In an embodiment, in Formulae 3 and 4, $R_{33}$ and $R_{43}$ may each independently be selected from hydrogen, a phenyl group, a naphthyl group, a biphenyl group, and a terphenyl group, but embodiments of the present disclosure are not limited thereto.

In Formulae 3 and 4, b33 and b43 may each independently be selected from 1, 2, 3, 4, 5, 6, 7, 8, 9, and 10.

In an embodiment, $X_{11}$ may be selected from groups represented by Formulae 3-1 to 3-3, and $X_{12}$ may be selected from groups represented by Formulae 4-1 to 4-3, but embodiments of the present disclosure are not limited thereto:

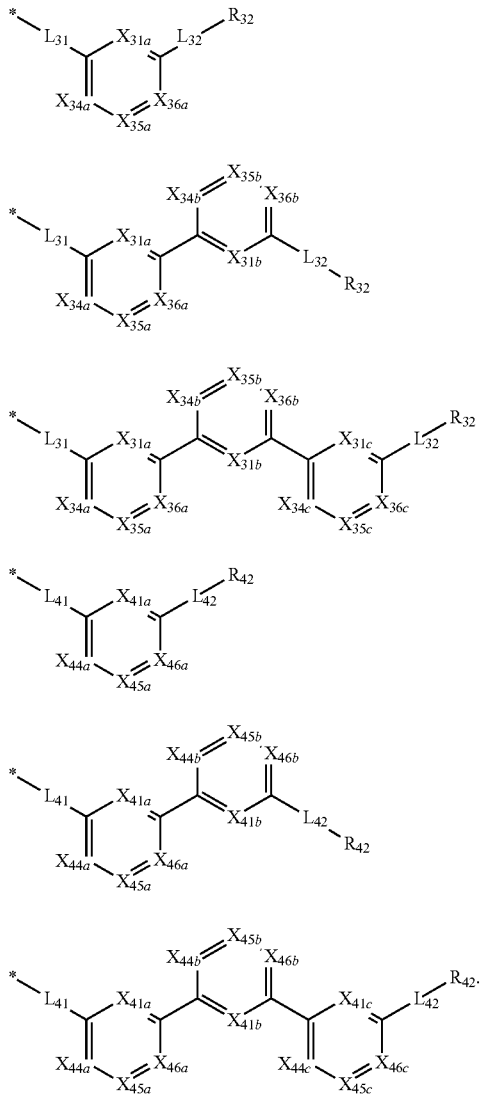

In Formulae 3-1 to 3-3 and 4-1 to 4-3, $L_{31}$, $L_{32}$, and $R_{32}$ may each independently be the same as described in Formula 3, $L_{41}$, $L_{42}$, and $R_{42}$ may each independently be the same as described in Formula 4, $X_{31a}$ to $X_{31c}$ may each independently be the same as described in connection with $X_{31}$ in Formula 3, $X_{41a}$ to $X_{41c}$ may each independently be the same as described in connection with $X_{41}$ in Formula 4, $X_{34a}$ may be selected from N and $C(R_{34a})$, $X_{34b}$ may be selected from N and $C(R_{34b})$, and $X_{34c}$ may be selected from N and $C(R_{34c})$, $X_{35a}$ may be selected from N and $C(R_{35a})$, $X_{35b}$ may be selected from N and $C(R_{35b})$, and $X_{35c}$ may be selected from N and $C(R_{35c})$, $X_{36a}$ may be selected from N and $C(R_{36a})$, $X_{36b}$ may be selected from N and $C(R_{36b})$, and $X_{36c}$ may be selected from N and $C(R_{36c})$, $X_{44a}$ may be selected from N and $C(R_{44a})$, $X_{44b}$ may be selected from N and $C(R_{44b})$, and $X_{44c}$ may be selected from N and $C(R_{34c})$, $X_{45a}$ may be selected from N and $C(R_{45a})$, $X_{45b}$ may be selected from N and $C(R_{45b})$, and $X_{45c}$ may be selected from N and $C(R_{45c})$, $X_{46a}$ may be selected from N and $C(R_{46a})$, $X_{46b}$ may be selected from N and $C(R_{46b})$, and $X_{46c}$ may be selected from N and $C(R_{46c})$, $R_{34a}$ to $R_{34c}$, $R_{35a}$ to $R_{35c}$, and $R_{36a}$ to $R_{36c}$ may each independently be the same as described in connection with $R_{33}$ in Formula 3, $R_{44a}$ to $R_{44c}$, $R_{45a}$ to $R_{45c}$, and $R_{46a}$ to $R_{46c}$ may each independently be the same as described in connection with $R_{43}$ in Formula 4, and

* indicates a binding site to a neighboring atom.

In one or more embodiments, in Formula 1, $X_{11}$ may be selected from groups represented by Formulae 3-2 and 3-3, $X_{12}$ may be selected from groups represented by Formulae 4-2 and 4-3, but embodiments of the present disclosure are not limited thereto.

In one or more embodiments, in Formula 1, $X_{11}$ may be a group represented by Formula 3-2, and $X_{12}$ may be a group represented by Formula 4-2; or $X_{11}$ may be a group represented by Formula 3-3, and $X_{12}$ may be a group represented by Formula 4-3, but embodiments of the present disclosure are not limited thereto.

In one or more embodiments, the condensed cyclic compound may be represented by one selected from Formulae 1-1 and 1-2, but embodiments of the present disclosure are not limited thereto:

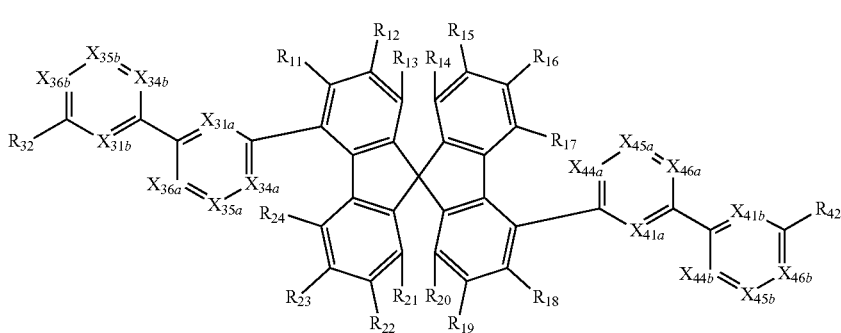

1-1

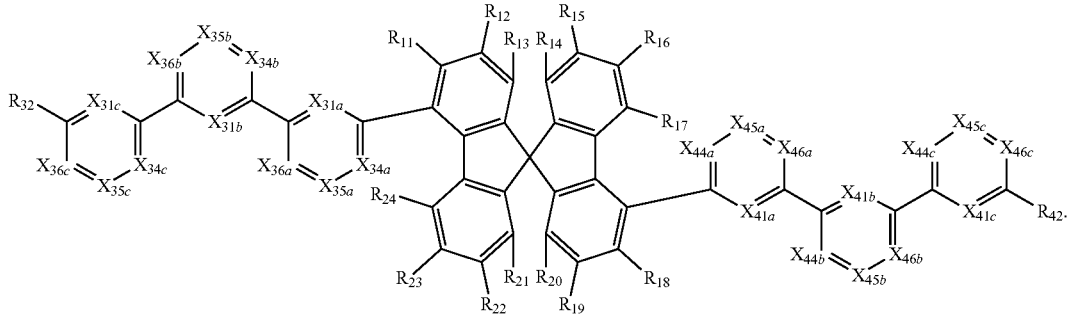

1-2

In Formulae 1-1 and 1-2, $R_{11}$ to $R_{24}$, $R_{32}$, and $R_{42}$ may each independently be the same as described in Formula 1, $X_{31a}$ to $X_{31c}$ may each independently be the same as described in connection with $X_{31}$ in Formula 3, $X_{41a}$ to $X_{41c}$ may each independently be the same as described in connection with $X_{41}$ in Formula 4, $X_{34a}$ may be selected from N and $C(R_{34a})$, $X_{34b}$ may be selected from N and $C(R_{34b})$, and $X_{34c}$ may be selected from N and $C(R_{34c})$, $X_{35a}$ may be selected from N and $C(R_{35a})$, $X_{35b}$ may be selected from N and $C(R_{35b})$, and $X_{35c}$ may be selected from N and $C(R_{35c})$, $X_{36a}$ may be selected from N and $C(R_{36a})$, $X_{36b}$ may be selected from N and $C(R_{36b})$, and $X_{36c}$ may be selected from N and $C(R_{36c})$, $X_{44a}$ may be selected from N and $C(R_{44a})$, $X_{44b}$ may be selected from N and $C(R_{44b})$, and $X_{44c}$ may be selected from N and $C(R_{34c})$, $X_{45a}$ may be selected from N and $C(R_{45a})$, $X_{45b}$ may be selected from N and $C(R_{45b})$, and $X_{45c}$ may be selected from N and $C(R_{45c})$, $X_{46a}$ may be selected from N and $C(R_{46a})$, $X_{46b}$ may be selected from N and $C(R_{46b})$, and $X_{46c}$ may be selected from N and $C(R_{46c})$, $R_{34a}$ to $R_{34c}$, $R_{35a}$ to $R_{35c}$, and $R_{36a}$ to $R_{36c}$ may each independently be the same as described in connection with $R_{33}$ in Formula 3, and $R_{44a}$ to $R_{44c}$, $R_{45a}$ to $R_{45c}$, and $R_{46a}$ to $R_{46c}$ may each independently be the same as described in connection with $R_{43}$ in Formula 4.

In one or more embodiments, the condensed cyclic compound may be selected from Compounds 1 to 16, but embodiments of the present disclosure are not limited thereto:

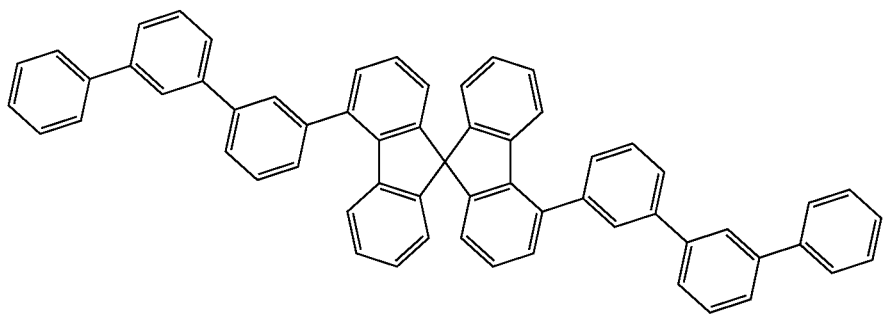

1

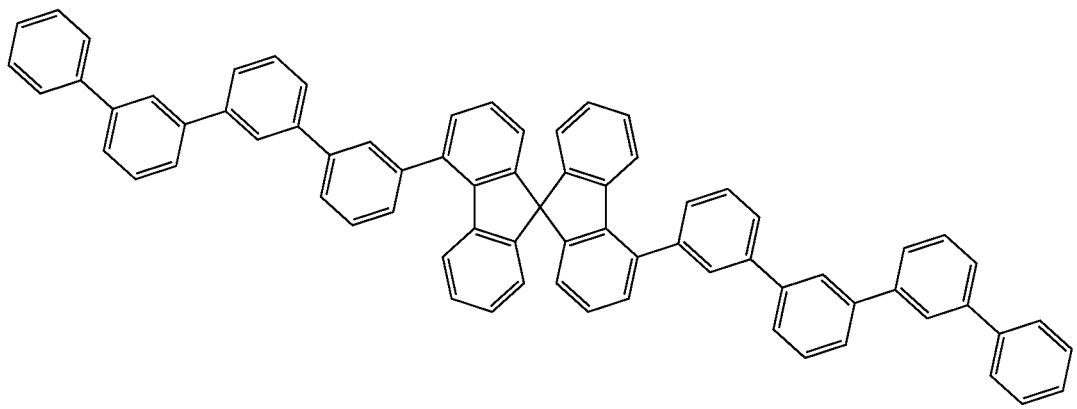

2

-continued
3
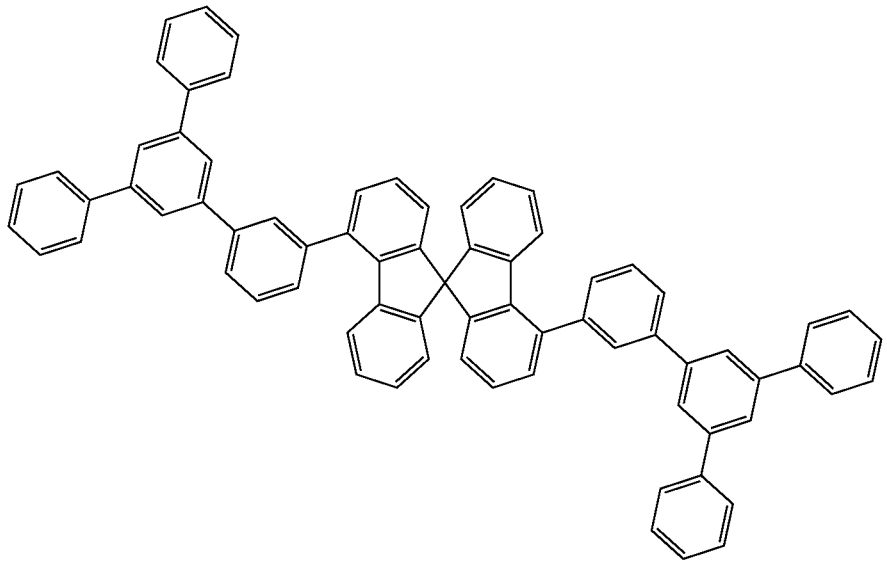
4
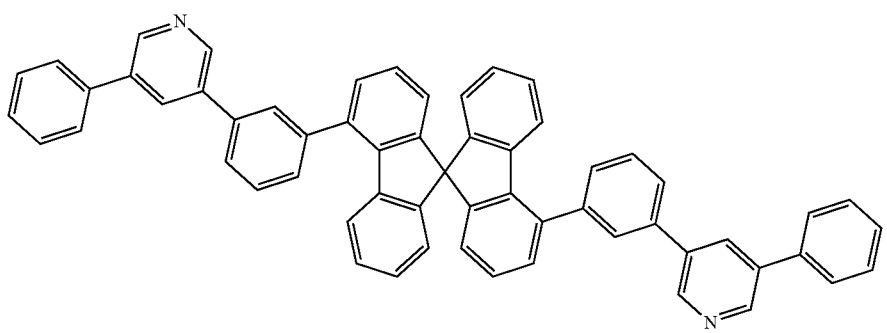
5
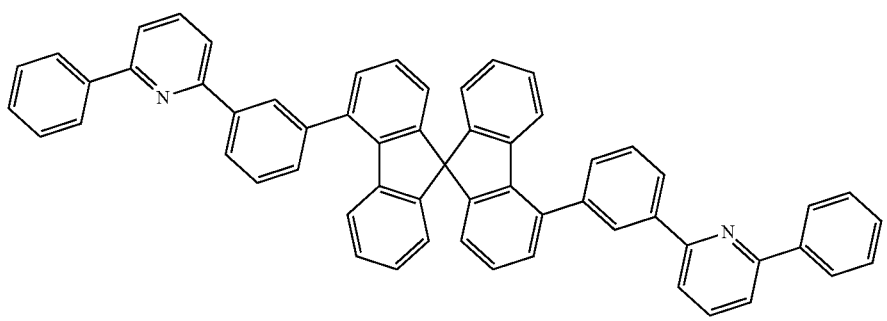
6
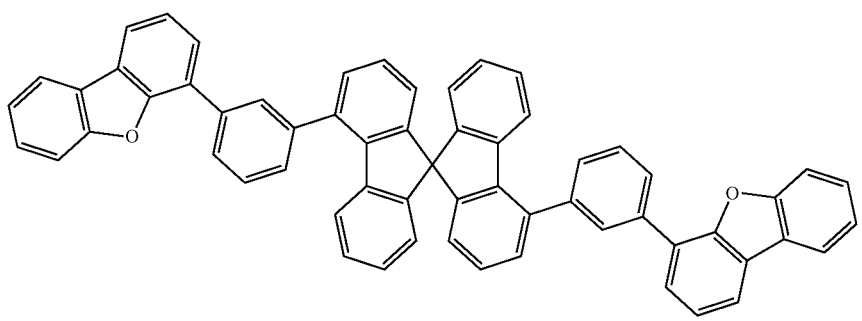

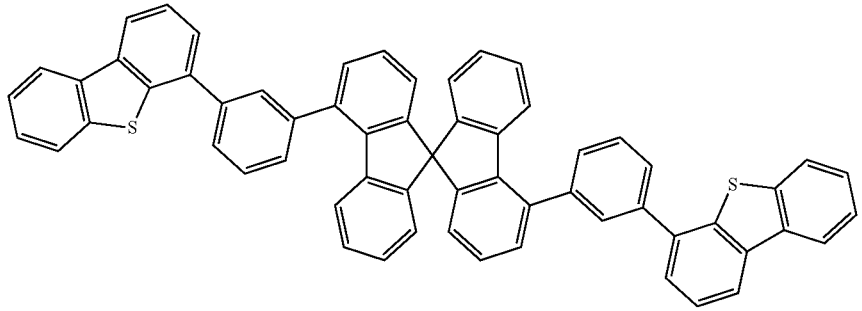

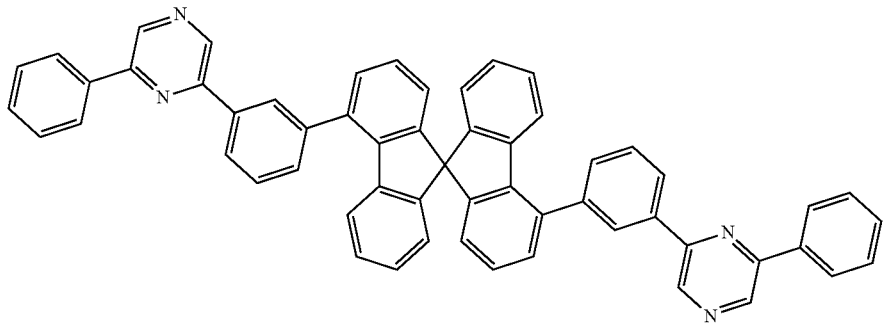
11
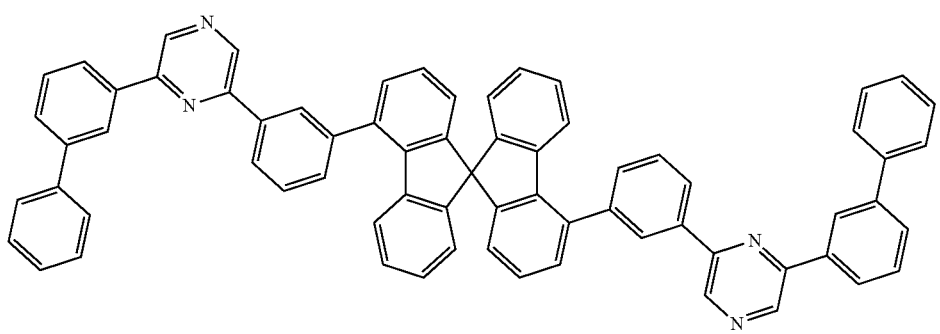
12
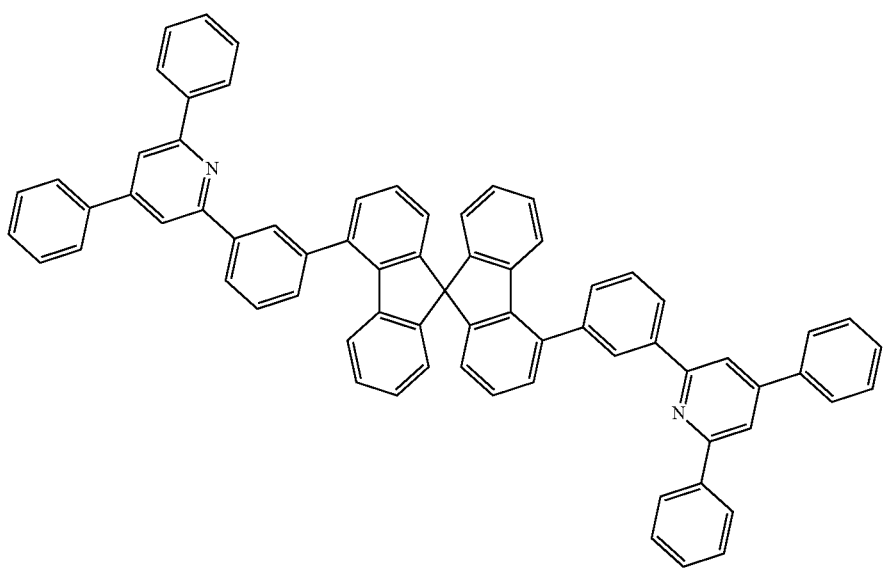
13

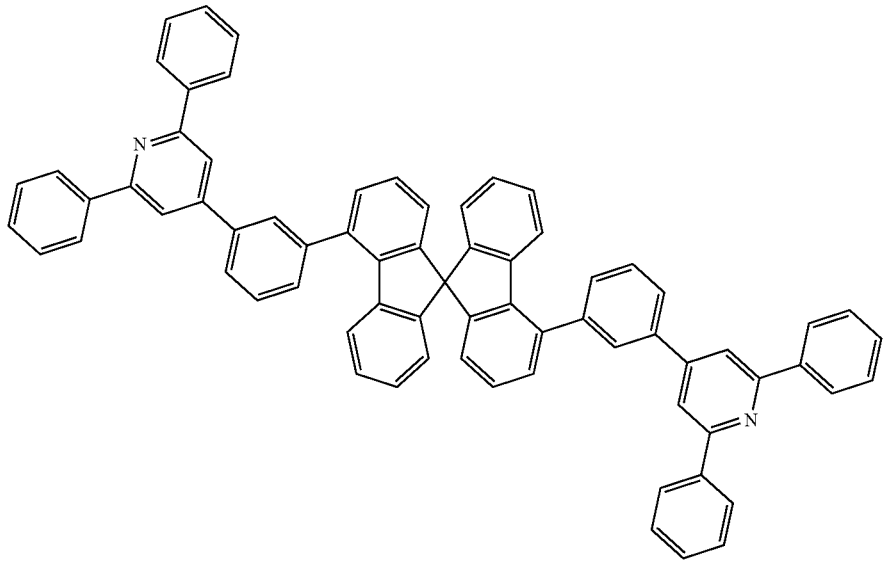
14
15

-continued

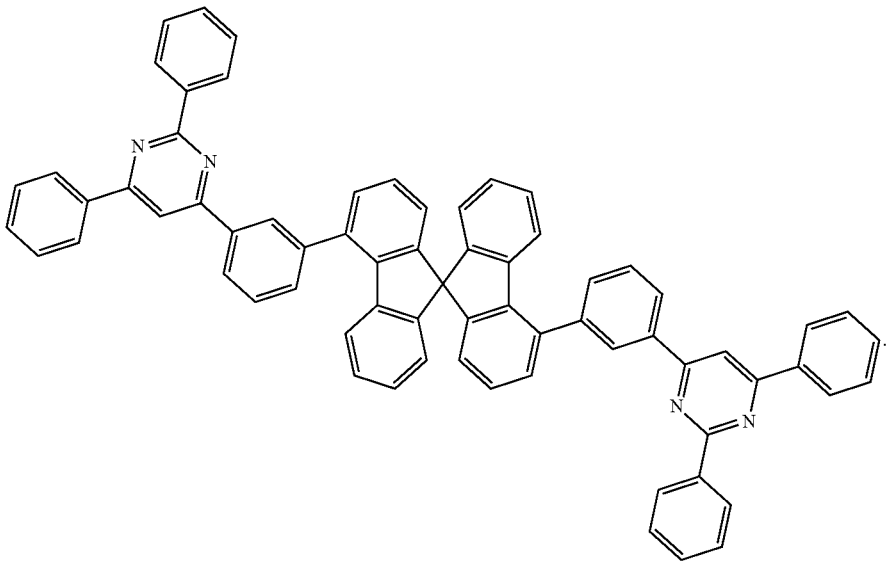

Since the condensed cyclic compound represented by Formula 1 includes a spiro-bifluorene core having a distorted structure, π-π stacking is suppressed, and thus, aggregation between compounds may be suppressed. Since the aggregation is suppressed, the condensed cyclic compound represented by Formula 1 may have excellent solubility in a solvent. When a layer is formed by solution process, the aggregation between the condensed cyclic compounds is suppressed, thereby providing a film having improved film-forming properties.

Therefore, even when the organic light-emitting device is manufactured by using solution coating, it is possible to maintain or improve the performance of the organic light-emitting device. Therefore, the organic light-emitting device may be manufactured without expensive vacuum deposition. For example, it may be advantageous to manufacturing a large-area organic light-emitting device.

In addition, since the condensed cyclic compound represented by Formula 1 has a high lowest excitation triplet energy level and high charge mobility, hole transport capability and/or electron transport capability may be excellent.

Because the condensed cyclic compound represented by Formula 1 includes an asymmetric meta-linking substituent, such as $X_{11}$ and $X_{12}$, at 4 and 4' positions of spiro-bifluorene, a rotational isomer may be generated. Therefore, the number of conformations may increase and amorphous properties may be improved. Therefore, the solubility to the solvent may be improved, and the crystals of the condensed cyclic compound are not precipitated in a solution state for a longer time. In addition, when a film is manufactured through a coating process by using a solution including the condensed cyclic compound, physical defects such as protrusions or pin holes may be reduced.

The condensed cyclic compound represented by Formula 1 may be included in a pair of electrodes of an organic light-emitting device. For example, the condensed cyclic compound represented by Formula 1 may be included in an emission layer, and may be suitable as a host.

The condensed cyclic compound represented by Formula 1 may be synthesized by using a known organic synthesis method. A specific method of synthesizing the condensed cyclic compound represented by Formula 1 can be understood by those of ordinary skill in the art by referring to Examples provided below.

Composition

Hereinafter, a composition according to an embodiment will be described in detail.

The composition may include at least one of the condensed cyclic compound described above.

For example, the composition may further include at least one selected from a first compound represented by Formula 5 and a second compound represented by Formula 6:

Formula 5
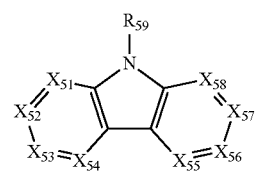

Formula 6
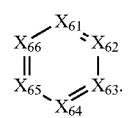

In Formulae 5 and 6, $X_{51}$ may be N or $C(R_{51})$; $X_{52}$ may be N or $C(R_{52})$; $X_{53}$ may be N or $C(R_{53})$; $X_{54}$ may be N or $C(R_{54})$; $X_{55}$ may be N or $C(R_{55})$; $X_{56}$ may be N or $C(R_{56})$; $X_{57}$ may be N or $C(R_{57})$; and $X_{5a}$ may be N or $C(R_{58})$, $X_{61}$ may be N or $C(R_{61})$; $X_{62}$ may be N or $C(R_{62})$; $X_{63}$ may be N or $C(R_{63})$; $X_{64}$ may be N or $C(R_{64})$; $X_{65}$ may be N or $C(R_{65})$; and $X_{66}$ may be N or $C(R_{66})$, wherein at least one selected from $X_{61}$ to $X_{66}$ is N, $R_{51}$ to $R_{58}$ and $R_{61}$ to $R_{66}$ may each independently be selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{59}$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, at least one selected from $R_{61}$ to $R_{66}$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 5 and 6, two neighboring groups selected from $R_{51}$ to $R_{58}$ and $R_{61}$ to $R_{66}$ may optionally be linked to form a ring, but embodiments of the present disclosure are not limited thereto.

The first compound has the shallowest highest occupied molecular orbital (HOMO) level, except for the light-emitting material (dopant) among the compounds included in the composition. Therefore, the first compound has high hole injection capability and/or hole transport capability.

Therefore, the hole injection capability and/or hole transport capability of the composition may be adjusted by adjusting the ratio that the first compound occupies within the composition. Hence, it is possible to easily control the hole density profile according to the amount of the host and the thickness direction of the emission layer in the organic light-emitting device including the composition.

The second compound has the deepest lowest unoccupied molecular orbital (LUMO) level among the compounds included in the composition. Therefore, the second compound has high electron injection capability and/or electron transport capability.

Therefore, the electron injection capability and/or electron transport capability of the composition may be adjusted by adjusting the ratio that the second compound occupies within the composition. Hence, it is possible to easily control the electron density profile according to the amount of the electron and the thickness direction of the emission layer in the organic light-emitting device including the composition.

When the composition includes the condensed cyclic compound and the first compound, the composition may have excellent hole injection capability and/or hole transport capability, and the composition may be used for the hole injection layer, the hole transport layer, and/or the emission layer of the organic light-emitting device.

When the composition includes the condensed cyclic compound and the second compound, the composition may have excellent electron injection capability and/or electron transport capability, and the composition may be used for the electron injection layer, the electron transport layer, and/or the emission layer of the organic light-emitting device.

When the composition includes the condensed cyclic compound, the first compound, and the second compound, the composition may have excellent hole injection capability, hole transport capability, electron injection capability, and/or electron transport capability, and the composition may be used for the hole injection layer, the hole transport layer, the emission layer, the electron transport layer, and/or the electron injection layer of the organic light-emitting device.

In an embodiment, the composition may include the first compound and the second compound, but embodiments of the present disclosure are not limited thereto.

When the composition includes both the first compound and the second compound, the control for holes and the control for electrons may be each independently performed.

Therefore, work convenience may be increased in the process of optimizing the performance of the organic light-emitting device including the composition.

The composition may further include a light-emitting material.

The light-emitting material is not particularly limited as long as the light-emitting material has a light-emitting function. The light-emitting material may be a fluorescent dopant, a phosphorescent dopant, a quantum dot, or the like.

The fluorescent dopant is a compound that can emit light from singlet exciton. For example, the fluorescent dopant may be a perlene and a derivative thereof, a rubrene and a derivative thereof, a coumarin and a derivative thereof, or a 4-dicyanomethylene-2-(p-dimethylaminostyryl)-6-methyl-4H-pyran (DCM) and a derivative thereof, but embodiments of the present disclosure are not limited thereto.

The phosphorescent dopant is a compound that can emit light from triplet exciton, and may be an organometallic compound. For example, the phosphorescent dopant may be an iridium complex, such as bis[2-(4,6-difluorophenyl) pyridinate] picolinate iridium(III) (FIrpic), bis(1-phenylisoquinoline)(acetylacetonate) iridium(III) (Ir(piq)$_2$(acac)), tris (2-phenylpyridine) iridium(III) (Ir(ppy)$_3$), or tris(2-(3-p-xylyl)phenyl)pyridine iridium(III) (dopant), an osmium complex, a platinum complex, or the like, but embodiments of the present disclosure are not limited thereto.

The quantum dot may be a nanoparticle including group II-VI semiconductor, group III-V semiconductor, or group IV-IV semiconductor. For example, the quantum dot may be CdO, CdS, CdSe, CdTe, ZnO, ZnS, ZnSe, ZnTe, HgS, HgSe, HgTe, MgSe, MgS CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaN, GaP, GaAs, AlN, AlP, AlAs, InN, InP, InAs, InSb, GaNP, GaNAs, GaNSb, GaPAs, GaPSb, AlNP, AlNAs, AlNSb, AlPAs, AlPSb, InNP, InNAs, InPAs, InPSb, GaAlNP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments of the present disclosure are not limited thereto. In addition, the diameter of the quantum dot is not particularly limited, but may be in a range of about 1 nanometer (nm) to about 20 nm. The quantum dot may be a single core structure, or may be a core-shell structure.

The composition may further include a solvent.

The solvent is not particularly limited as long as the condensed cyclic compound represented by Formula 1, the first compound represented by Formula 5, and/or the second compound represented by Formula 6 is dissolved therein. For example, the solvent may be toluene, xylene, ethylbenzene, diethylbenzene, mesitylene, propylbenzene, cyclohexylbenzene, dimethoxybenzene, anisole, ethoxytoluene, phenoxytoluene, iso-propylbiphenyl, dimethylanisole, phenyl acetate, phenyl propionic acid, methyl benzoate, ethyl benzoate, or the like, but embodiments of the present disclosure are not limited thereto.

The concentration of the composition is not particularly limited, and may be appropriately controlled according to the purpose thereof.

The concentration of the condensed cyclic compound represented by Formula 1 in the composition may be in a range of about 0.1 percent by weight (weight %) to about 10 weight %, for example, about 0.5 weight % to about 5 weight %, but embodiments of the present disclosure are not limited thereto. While not wishing to be bound by theory, it is understood that when the concentration of the condensed cyclic compound represented by Formula 1 in the composition is within this range, coatability may be improved.

In an embodiment, when the composition includes the condensed cyclic compound represented by Formula 1 and the first compound represented by Formula 5, the concentration of the condensed cyclic compound may be in a range of about 0.1 weight % to about 10 weight %, for example, about 0.5 weight % to about 5 weight %, and the concentration of the first compound may be in a range of about 0.1 weight % to about 10 weight %, for example, about 0.5 weight % to about 5 weight %.

In an embodiment, when the composition includes the condensed cyclic compound represented by Formula 1 and the second compound represented by Formula 6, the concentration of the condensed cyclic compound may be in a range of about 0.1 weight % to about 10 weight %, for example, about 0.5 weight % to about 5 weight %, and the concentration of the second compound may be in a range of about 0.1 weight % to about 10 weight %, for example, about 0.5 weight % to about 5 weight %.

In one or more embodiments, when the composition includes the condensed cyclic compound represented by Formula 1, the first compound represented by Formula 5, and the second compound represented by Formula 6, the concentration of the condensed cyclic compound may be in a range of about 0.1 weight % to about 10 weight %, for example, about 0.5 weight % to about 5 weight %, and the concentration of the first compound may be in a range of about 0.1 weight % to about 10 weight %, for example, about 0.5 weight % to about 5 weight %, and the concentration of the second compound may be in a range of about 0.1 weight % to about 10 weight %, for example, about 0.5 weight % to about 5 weight %.

Therefore, the composition may be used as the material for the light-emitting device (for example, an organic light-emitting device, a quantum dot light-emitting device, or the like). For example, the composition may be used for the emission layer, the charge injection layer, and/or the charge transport layer of the light-emitting diode.

For example, the composition may be used for the emission layer of the light-emitting device. For example, the composition may be used to manufacture the light-emitting device by using solution deposition. At this time, the current efficiency and light-emitting lifespan of the light-emitting device may be maintained or improved.

Organic Light-Emitting Device

Hereinafter, an organic light-emitting device according to an embodiment will be described in detail with reference to the FIGURE. The FIGURE is a schematic view of an organic light-emitting device according to an embodiment.

An organic light-emitting device 100 according to an embodiment may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The condensed cyclic compound represented by Formula 1 may be included in, for example, an organic layer disposed between the first electrode 120 and the second electrode 180 (for example, the hole injection layer 130, the hole transport layer 140, the emission layer 150, the electron transport layer 160, or the electron injection layer 170). In an embodiment, the condensed cyclic compound represented by Formula 1 may be included in the emission layer 150 as a host. Alternatively, the condensed cyclic compound represented by Formula 1 may be included in another organic layer other than the emission layer 150. For example, the condensed cyclic compound represented by Formula 1 may be included in the hole injection layer 130 and/or the hole transport layer 140 as a charge transport material.

The term "organic layer" as used herein refers to a single layer and/or a plurality of layers disposed between the first electrode and the second electrode of the organic light-emitting device. The "organic layer" may include, in addition to an organic compound, an organometallic compound including metal.

The expression "(an organic layer) includes at least one organometallic compound" as used herein includes an embodiment in which "(an organic layer) includes identical condensed cyclic compounds represented by Formula 1" and an embodiment in which "(an organic layer) includes two or more different condensed cyclic compounds represented by Formula 1."

For example, the organic layer may include, as the condensed cyclic compound, only Compound 1. In this regard, Compound 1 may be included in an emission layer of the organic light-emitting device. In one or more embodiments, the organic layer may include, as the condensed cyclic compound, Compound 1 and Compound 2. In this regard, Compound 1 and Compound 2 may be included in the same layer (for example, Compound 1 and Compound 2 may both be included in an emission layer).

The substrate 110 may be any substrate that is used in an organic light-emitting device according to the related art. The substrate 110 may be any substrate that is used in an organic light-emitting device according to the related art. For example, the substrate 110 may be a glass substrate, a silicon substrate, or a transparent plastic substrate, each having excellent mechanical strength, thermal stability, surface smoothness, ease of handling, and water resistance, but embodiments of the present disclosure are not limited thereto.

The first electrode 120 may be formed on the substrate 110. The first electrode 120 may be, for example, an anode, and may be formed of a material with a high work function to facilitate hole injection, such as an alloy or a conductive compound. The first electrode 120 may be a reflective electrode, a semi-transmissive electrode, or a transmissive electrode. The first electrode 120 may have a single-layered structure, or a multi-layered structure including two or more layers. For example, the first electrode 120 may be a transparent electrode formed of indium tin oxide (ITO), indium zinc oxide (IZO), tin oxide (SnO2), or zinc oxide (ZnO), which has excellent transparency and conductivity. On the transparent first electrode 120, magnesium (Mg), aluminum (Al), aluminum-lithium (Al—Li), calcium (Ca), magnesium-indium (Mg—In), or magnesium-silver (Mg—Ag) may be disposed, so as to form a reflective electrode. In an embodiment, the first electrode 120 may have a three-layered structure of ITO/Ag/ITO, but embodiments of the present disclosure are not limited thereto.

The hole transport region may be disposed on the first electrode 120.

The hole transport region may include at least one selected from selected from a hole injection layer 130, a hole transport layer 140, an electron blocking layer (not shown), and a buffer layer (not shown).

The hole transport region may include only either a hole injection layer 130 or a hole transport layer 140. In an embodiment, the hole transport region may have a hole injection layer/hole transport layer structure or a hole injection layer/hole transport layer/electron blocking layer structure, wherein for each structure, constituting layers are sequentially stacked from the first electrode 120 in the stated order.

The hole injection layer 130 may include at least one selected from, for example, poly(ether ketone)-containing triphenylamine (TPAPEK), 4-iso-propyl-4'-methyldiphenyliodonium tetrakis(pentafluorophenyl) borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4"-tris(3-methylphenylphenylamino) triphenylamine (m-MTDATA), N,N'-di(1-naphthyl)-N,N'-diphenylbenzidine (NPB), 4,4',4"-tris(diphenylamino) triphenylamine (TDATA), 4,4',4"-tris(N,N-2-naphthylphenylamino) triphenylamine (2-TNATA), polyaniline/dodecylbenzene sulphonic acid (PANI/DBSA), poly(3,4-ethylenedioxythiophene)/poly(4-styrene sulfonate) (PEDOT/PSS), polyaniline/10-camphor sulfonic acid (PANI/CSA), and polyaniline/poly(4-styrene sulfonate) (PAN I/PSS).

The hole injection layer 130 may have a thickness in a range of about 10 nm to about 1,000 nm, for example, about 10 nm to about 100 nm.

The hole transport layer 140 may include at least one selected from selected from, for example, a carbazole derivative, such as 1,1-bis[(di-4-tolylamino)phenyl]cyclohexane (TAPC), N-phenylcarbazole, and polyvinylcarbazole, N,N'-bis(3-methylphenyl)-N,N'-diphenyl-[1,1-biphenyl]-4,4'-diamine (TPD), 4,4',4"-tris(N-carbazolyl) triphenylamine (TCTA), N,N'-di(1-naphthyl)-N,N'-diphenylbenzidine (NPB), poly(9,9-dioctyl-fluorene-co-N-(4-butylphenyl)-diphenylamine (TFB), and amine-based polymer.

The hole transport layer 140 may have a thickness in a range of about 10 nm to about 1,000 nm, for example, about 10 nm to about 150 nm.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or Compound HT-D2 below, but are not limited thereto.

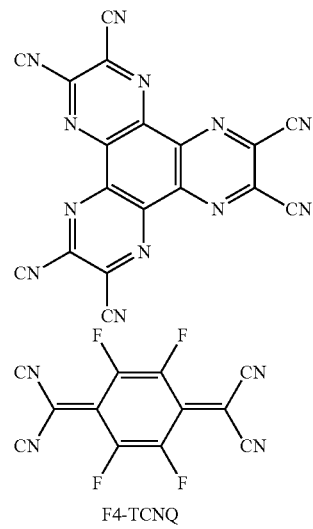

HT-D1

F4-TCNQ

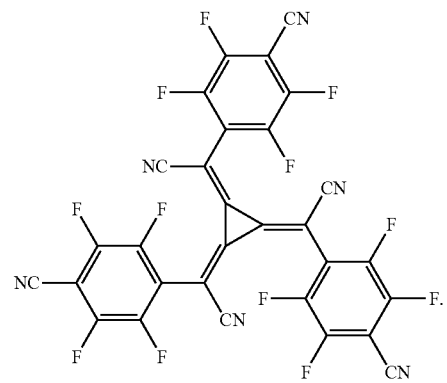

HT-D2

Meanwhile, when the hole transport region includes a buffer layer, a material for the buffer layer may be selected from materials for the hole transport region described above and materials for a host to be explained later, but embodiments of the present disclosure are not limited thereto.

In addition, when the hole transport region includes an electron blocking layer, a material for the electron blocking layer may be selected from materials for the hole transport region described above and materials for a host to be explained later, but embodiments of the present disclosure are not limited thereto. For example, when the hole transport region includes an electron blocking layer, a material for the electron blocking layer may be mCP.

The emission layer 150 may be formed on the hole transport region. The emission layer 150 is a layer that emits light by fluorescence or phosphorescence. The emission layer 150 may include a host and/or a dopant, and when included, the host may include the condensed cyclic compound represented by Formula 1. In addition, the host and/or the dopant included in the emission layer 150 may be known materials.

For example, the host may include tris(8-quinolinato) aluminium ($Alq_3$), 4,4'-bis(carbazol-9-yl)biphenyl (CBP), poly(n-vinylcarbazole) (PVK), 9,10-di(naphthalene)anthracene (ADN), 4,4',4"-tris(N-carbazolyl)triphenylamine (TCTA), 1,3,5-tris(N-phenyl-benzimidazol-2-yl)benzene (TPBi), 3-tert-butyl-9,10-di(naphth-2-yl)anthracene (TBADN), distyrylarylene (DSA), and 4,4'-bis(9-carbazole)-2,2'-dimethyl-bipheny (dmCBP), but embodiments of the present disclosure are not limited thereto.

In an embodiment, the host may include a first compound represented by Formula 5, but embodiments of the present disclosure are not limited thereto:

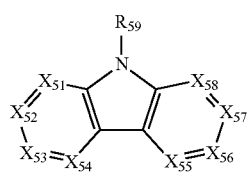

Formula 5

In Formula 5, $X_{51}$ may be N or $C(R_{51})$; $X_{52}$ $X_{51}$ may be N or $C(R_{52})$; $X_{53}$ $X_{51}$ may be N or $C(R_{53})$; $X_{54}$ $X_{51}$ may be N or $C(R_{54})$; $X_{55}$ $X_{51}$ may be N or $C(R_{55})$; $X_{56}$ $X_{51}$ may be N or $C(R_{56})$; $X_{57}$ $X_{51}$ may be N or $C(R_{57})$; and $X_{58}$ $X_{51}$ may be N or $C(R_{58})$, $R_{51}$ to $R_{58}$ may each independently be selected from hydrogen, deuterium, a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group, and $R_{59}$ may be selected from a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group.

In an embodiment, the first compound may be Compound H1, but embodiments of the present disclosure are not limited thereto:

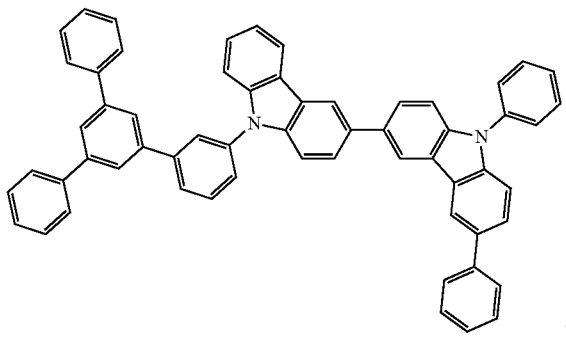

H1

In one or more embodiments, the host may include a second compound represented by Formula 6, but embodiments of the present disclosure are not limited thereto:

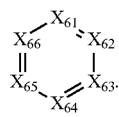

Formula 6

In Formula 6, $X_{61}$ may be N or $C(R_{61})$; $X_{62}$ may be N or $C(R_{62})$; $X_{63}$ may be N or $C(R_{63})$; $X_{64}$ may be N or $C(R_{64})$; $X_{65}$ may be N or $C(R_{65})$; and $X_{66}$ may be N or $C(R_{66})$, wherein at least one selected from $X_{61}$ to $X_{66}$ may be N, $R_{61}$ to $R_{66}$ may each independently be selected from hydrogen, deuterium, a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group, at least one selected from $R_{61}$ to $R_{66}$ may be selected from a substituted or unsubstituted $C_6$-$C_{30}$ aryl group, a substituted or unsubstituted $C_1$-$C_{30}$ heteroaryl group, a substituted or unsubstituted monovalent non-aromatic condensed polycyclic group, and a substituted or unsubstituted monovalent non-aromatic condensed heteropolycyclic group.

In an embodiment, the second compound may be Compound E1, but embodiments of the present disclosure are not limited thereto:

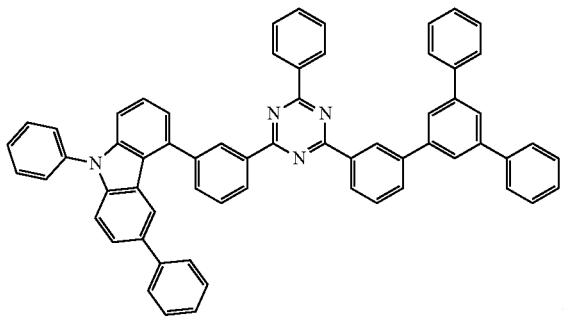

E1

For example, the dopant may include a perylene and a derivative thereof, a rubrene and a derivative thereof, a coumarin and a derivative thereof, 4-dicyanomethylene-2-(p-dimethylaminostyryl)-6-methyl-4H-pyran (DCM) and a derivative thereof, bis[2-(4,6-difluorophenyl)pyridinate] picolinate iridium (III) (FIrpic), an iridium complex, such as bis(1-phenylisoquinoline)(acetylacetonate) iridium (III) (Ir(piq)$_2$(acac)), tris(2-phenylpyridine) iridium (III) (Ir(ppy)$_3$) or tris(2-(3-p-xylyl)phenyl)pyridine iridium (III) (dopant), an osmium complex, or a platinum complex, but embodiments of the present disclosure are not limited thereto.

When the emission layer includes a host and a dopant, an amount of the dopant may be about 0.01 parts by weight to about 15 parts by weight based on 100 parts by weight of the host material, but embodiments of the present disclosure are not limited thereto.

The emission layer 150 may have a thickness in a range of about 10 nm to about 60 nm.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The hole transport region may be disposed on the emission layer 150.

The electron transport region may include at least one selected from a hole blocking layer (not shown), an electron transport layer 160, and an electron injection layer 170.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

For example, the organic light-emitting device 100 may include, to prevent the excitons or holes from diffusing into the electron transport layer 160, a hole blocking layer disposed between the electron transport layer 160 and the emission layer 150.

The hole blocking layer may include, for example, at least one selected from an oxadiazole derivative, a triazole derivative, BCP, Bphen, BAlq, and HB1, but embodiments of the present disclosure are not limited thereto:

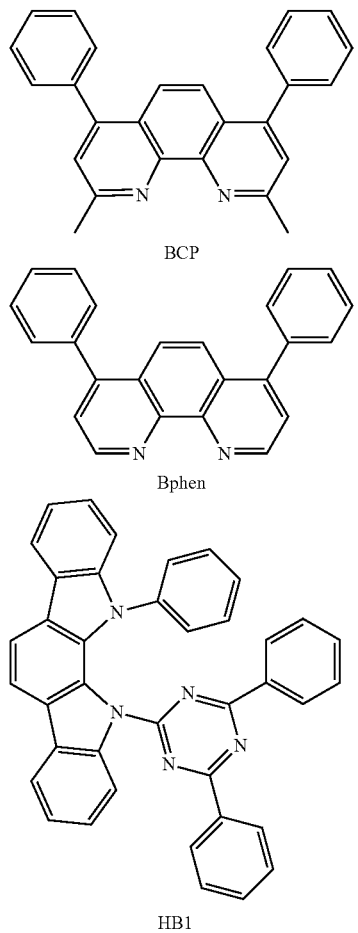

A thickness of the hole blocking layer may be in a range of about 2 nm to about 100 nm, for example, about 3 nm to about 30 nm. While not wishing to be bound by theory, it is understood that when the thickness of the hole blocking layer is within these ranges, the hole blocking layer may have excellent hole blocking characteristics without a substantial increase in driving voltage.

The electron transport layer 160 may include a tris(8-quinolinato) aluminium ($Alq_3$), BAlq, a compound including a pyridine ring, such as 1,3,5-tri[(3-pyridyl)-phen-3-yl] benzene, a compound including a triazine ring, such as 2,4,6-tris(3'-(pyridin-3-yl)biphenyl-3-yl)-1,3,5-triazine, a compound including an imidazole ring, such as 2-(4-(N-phenylbenzimidazolyl-1-yl-phenyl)-9,10-dinaphthylanthracene, a compound including a triazole ring, such as TAZ and NTAZ, 1,3,5-tris(N-phenyl-benzimidazol-2-yl)benzene (TPBi), BCP, or Bphen:

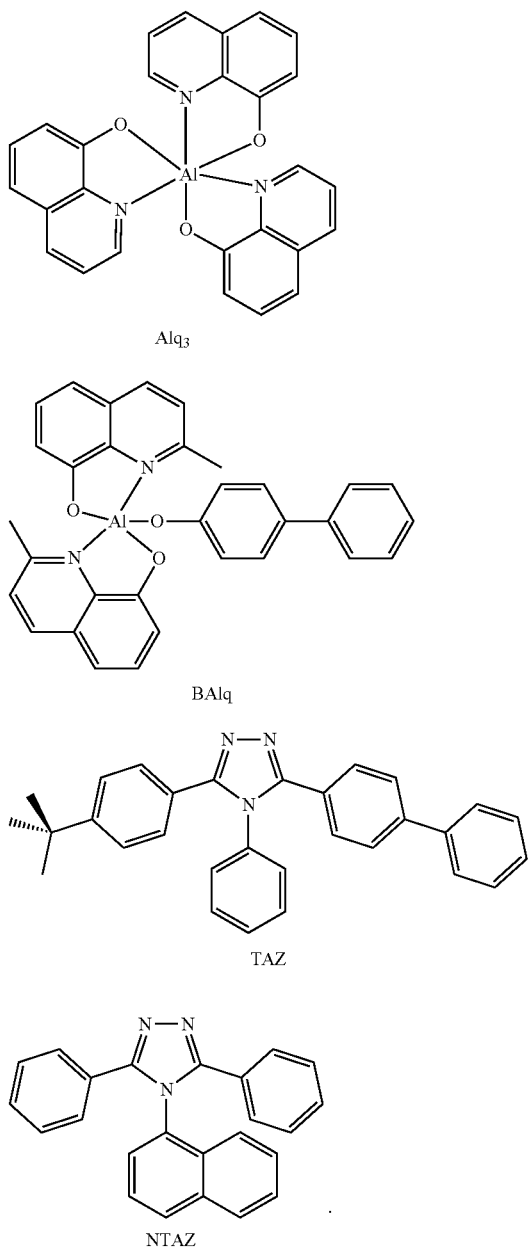

In one or more embodiments, the electron transport layer 160 may include a commercial product, such as KLET-01, KLET-02, KLET-03, KLET-10, or KLET-M1 (these products are available from Chemipro Kasei).

The electron transport layer 160 may further include, in addition to the materials described above, a metal-containing material.

The metal-containing material may include a Li complex. The Li complex may include, for example, Compound ET-D1 (lithium 8-hydroxyquinolate, LiQ) or ET-D2:

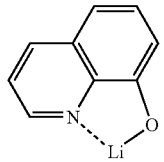

ET-D1

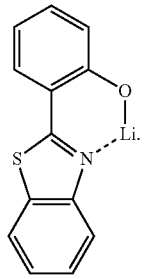

ET-D2

The electron transport layer 160 may be formed to a thickness, for example, in a range of about 15 nm to about 50 nm.

The electron injection layer 170 may be formed on the electron transport layer 160.

The electron injection layer 170 may include, for example, an lithium compound, such as (8-hydroxyquinolinato)lithium (LiQ) and lithium fluoride (LiF), sodium chloride (NaCl), cesium fluoride (CsF), lithium oxide ($Li_2O$), or barium oxide (BaO).

The electron injection layer 170 may be formed to a thickness in a range of about 0.3 nm to about 9 nm.

The second electrode 180 may be formed on the electron injection layer 170. The second electrode 180 may be a cathode and may be formed by using a material having a low work function among a metal, an alloy, an electrically conductive compound, and any combination thereof. For example, the second electrode 180 may be formed as a reflective electrode by using a metal such as lithium (Li), magnesium (Mg), aluminum (Al), and calcium (Ca), or an alloy such as aluminum-lithium (Al—Li), magnesium-indium (Mg—In), and magnesium-silver (Mg—Ag). Alternatively, the second electrode 180 may be formed as a transparent electrode by using the metal or the alloy thin film having a thickness of 20 nm or less, or a transparent conductive film such as indium tin oxide ($In_2O_3$—$SnO_2$) and indium zinc oxide ($In_2O_3$—ZnO).

In addition, the stacked structure of the organic light-emitting device 100 according to the embodiment is not limited to the above-described stacked structure. The organic light-emitting device 100 according to the embodiment may be formed in other known stacked structures. For example, in the organic light-emitting device 100, at least one selected from the hole injection layer 130, the hole transport layer 140, the electron transport layer 160, and the electron injection layer 170 may be omitted. The organic light-emitting device 100 may further include another layer. In addition, each layer of the organic light-emitting device 100 may be a single layer or a multi-layer.

A method of manufacturing each layer of the organic light-emitting device 100 according to the embodiment is not particularly limited. For example, each layer of the organic light-emitting device 100 according to the embodiment may be manufactured by using various methods, such as vacuum deposition, solution process, and Langmuir-Blodgett (LB) deposition.

The solution process may include spin coating, casting, micro gravure coating, gravure coating, bar coating, roll coating, wire bar coating, dip coating, spry coating, screen printing, flexographic printing, offset printing, and ink-jet printing.

Examples of the solvent used in the solution process may include toluene, xylene, diethyl ether, chloroform, ethyl acetate, dichloromethane, tetrahydrofuran, acetone, acetonitrile, N,N-dimethylformamide, dimethylsulfoxide, anisole, hexamethylphosphoric acid triamide, 1,2-dichloroethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, 1,2-hexanediol, methanol, ethanol, propanol, iso-propanol, cyclohexanal, and N-methyl-2-pyrrolidone, but the solvent is not limited as long as the solvent can dissolve the material used to form each layer.

Considering the coatability, the concentration of the composition used in the solution process may be in a range from about 0.1 weight % to about 10 weight %, for example, in a range from about 0.5 weight % to about 5 weight %, but embodiments of the present disclosure are not limited thereto.

The compound used in the vacuum deposition may be different according to the structure and thermal characteristics of the target layer, but may be selected from, for example, a deposition temperature of about 100° C. to about 500° C., a vacuum degree of about $10^{-8}$ torr to about $10^{-3}$ torr, a deposition rate of about 0.01 Angstroms per second (Å/sec) to about 100 Å/sec.

In an embodiment, the first electrode 120 may be an anode, and the second electrode 180 may be a cathode.

For example, the first electrode 120 may be an anode; the second electrode 180 may be a cathode; the organic layer may include the emission layer 150 disposed between the first electrode 120 and the second electrode 180; the organic layer may further include a hole transport region disposed between the first electrode 120 and the emission layer 150 and an electron transport region disposed between the emission layer 150 and the second electrode 180; the hole transport region may include at least one selected from a hole injection layer 130, a hole transport layer 140, a buffer layer, and an electron blocking layer; and the electron transport region may include at least one selected from a hole blocking layer, an electron transport layer 160, and an electron injection layer 170.

In one or more embodiments, the first electrode 120 may be a cathode, and the second electrode 180 may be an anode.

Hereinbefore, the organic light-emitting device has been described with reference to the FIGURE, but embodiments of the present disclosure are not limited thereto.

Description of Substituents

The expression "X and Y may each independently be" as used herein refers to a case where X and Y may be identical to each other, or a case where X and Y may be different from each other.

The term "substituted" as used herein refers to a case where hydrogen of a substituent such as $R_{11}$ may be further substituted with other substituents.

The term "$C_1$-$C_{24}$ alkyl group" as used herein refers to a linear or branched aliphatic saturated hydrocarbon monovalent group having 1 to 24 carbon atoms, and examples thereof include a methyl group, an ethyl group, an n-propyl group, an iso-propyl group, an n-butyl group, an iso-butyl group, a sec-butyl group, a tert-butyl group, an n-pentyl group, an iso-pentyl group, a tert-pentyl group, a neo-pentyl group, a 1,2-dimethylpropyl group, an n-hexyl group, an iso-hexyl group, a 1,3-dimethylbutyl group, a 1-iso-propylpropyl group, a 1,2-dimethylbutyl group, an n-heptyl group, a 1,4-dimethylpentyl group, 3-ethylpentyl group, a 2-methyl-1-iso-propylpropyl group, a 1-ethyl-3-methylbutyl group, an n-octyl group, a 2-ethylhexyl group, a 3-methyl-1-iso-propylbutyl group, a 2-methyl-1-iso-propyl group, a 1-tert-butyl-2-methylpropyl group, an n-nonyl group, a 3,5,5-trimethyldecyl group, an n-decyl group, an isodecyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, and an n-tetracosyl group.

The term "$C_1$-$C_{24}$ alkylene group" as used herein refers to a divalent group having the same structure as the $C_1$-$C_{24}$ alkyl group.

The term "$C_1$-$C_{24}$ alkoxy group" as used herein refers to a monovalent group represented by —$OA_{101}$ (wherein $A_{101}$ is the $C_1$-$C_{24}$ alkyl group), and examples thereof include a methoxy group, an ethoxy group, a propoxy group, an iso-propoxy group, an n-butoxy group, an iso-butoxy group, a sec-butoxy group, a tert-butoxy group, an n-pentoxy group, an iso-pentoxy group, a tert-pentoxy group, a neo-pentoxy group, an n-hexyloxy group, an iso-hexyloxy group, a heptyloxy group, an octyloxy group, a nonyloxy group, a decyloxy group, an undeoxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, and a 3-ethylpentyloxy group.

The term "$C_1$-$C_{24}$ alkylthio group" as used herein refers to a monovalent group represented by —$SA_{102}$ (wherein $A_{102}$ is the $C_1$-$C_{24}$ alkyl group).

The term "$C_3$-$C_{30}$ cycloalkyl group" as used herein refers to a monovalent saturated hydrocarbon monocyclic group having 3 to 30 carbon atoms involved in the ring formation, and examples thereof include a cyclopropyl group, a cyclobutyl group, a cyclopentyl group, a cyclohexyl group, and a cycloheptyl group. The term "$C_3$-$C_{30}$ cycloalkylene group" as used herein refers to a divalent group having the same structure as the $C_3$-$C_{30}$ cycloalkyl group.

The term "$C_6$-$C_{30}$ aryl group" as used herein refers to a monovalent group having a carbocyclic aromatic system having 6 to 30 carbon atoms involved in the ring formation (that is, when substituted with a substituent, the atom not included in the substituent is not counted as the carbon involved in the ring formation), and the term "$C_6$-$C_{30}$ arylene group" as used herein refers to a divalent group having a carbocyclic aromatic system having 6 to 30 carbon atoms. Examples of the $C_6$-$C_{30}$ aryl group are a phenyl group, a naphthyl group, an anthracenyl group, a phenanthrenyl group, a pyrenyl group, and a chrysenyl group. When the $C_6$-$C_{30}$ aryl group and the $C_6$-$C_{30}$ arylene group each include two or more rings, the rings may be fused to each other.

The term "$C_6$-$C_{30}$ aryloxy group" as used herein refers to a group represented by —$OA_{103}$ (wherein $A_{103}$ is the $C_6$-$C_{30}$ aryl group). Examples thereof include a 1-naphthyloxy group, a 2-naphthyloxy group, and a 2-azulenyloxy group.

The term "$C_6$-$C_{30}$ arylthio group" as used herein refers to a group represented by —$SA_{104}$ (wherein $A_{104}$ is the $C_6$-$C_{30}$ aryl group)

The term "$C_1$-$C_{30}$ heteroaryl group" as used herein refers to a monovalent group having a heterocyclic aromatic system that has at least one heteroatom selected from N, O, Si, P, and S as a ring-forming atom, and 1 to 30 carbon atoms. The term "$C_1$-$C_{30}$ heteroarylene group" as used herein refers to a divalent group having a heterocyclic aromatic system that has at least one heteroatom selected from N, O, Si, P, and S as a ring-forming atom, and 1 to 30 carbon atoms. Non-limiting examples of the $C_1$-$C_{30}$ heteroaryl group include a pyridinyl group, a pyrimidinyl group, a pyrazinyl group, a pyridazinyl group, a triazinyl group, a quinolinyl group, and an isoquinolinyl group. When the $C_5$-$C_{30}$ heteroaryl group and the $C_5$-$C_{30}$ heteroarylene group each include two or more rings, the rings may be fused to each other.

The term "$C_6$-$C_{30}$ heteroaryloxy group" as used herein refers to a group represented by —$SA_{102}$ (wherein $A_{102}$ is the $C_6$-$C_{30}$ heteroaryl group). Examples thereof include a 2-furanyloxy group, a 2-thienyloxy group, a 2-indolyloxy group, a 3-indolyloxy group, a 2-benzofuriloxy group, and a 2-benzothienyloxy group.

The term "$C_6$-$C_{30}$ heteroarylthio group" as used herein refers to a group represented by —$SA_{106}$ (wherein $A_{106}$ is the $C_6$-$C_{30}$ heteroaryl group).

The term "$C_7$-$C_{30}$ arylalkyl group" as used herein refers to an aryl group substituted with an alkyl group, and is a monovalent group in which the sum of carbon atoms in the alkyl group and the aryl group that constitute the $C_7$-$C_{30}$ arylalkyl group is in a range of 7 to 30. Examples of the $C_7$-$C_{30}$ aryl alkyl group include a benzyl group, a phenylethyl group, a phenylpropyl group, and a naphthylmethyl group.

The term "$C_7$-$C_{30}$ alkylheteroaryl group" as used herein refers to an alkyl group substituted with a heteroaryl group, and is a monovalent group in which the sum of carbon atoms in the alkyl group and the aryl group that constitute the $C_7$-$C_{30}$ alkylheteroaryl group is in a range of 7 to 30.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_6$-$C_{30}$ arene group" as used herein refers to an aromatic group having 6 to 30 carbon atoms only as ring-forming atoms. The term "$C_6$-$C_{30}$ arene group" as used herein refers to a monocyclic group or a polycyclic group, and, according to its chemical structure, may be a monovalent, divalent, trivalent, tetravalent, pentavalent, or hexavalent group.

The term "$C_1$-$C_{30}$ heteroarene group" as used herein refers to an aromatic group having, in addition to 1 to 30 carbon atoms as ring-forming atoms, at least one selected from hetero atom selected from N, O, P, Si, and S. The term "$C_1$-$C_{30}$ heteroarene group" as used herein refers to a monocyclic group or a polycyclic group, and, according to its chemical structure, may be a monovalent, divalent, trivalent, tetravalent, pentavalent, or hexavalent group.

The term "$C_5$-$C_{30}$ carbocyclic group" as used herein refers to a saturated or unsaturated cyclic group having, as a ring-forming atom, 5 to 30 carbon atoms only.

The term "$C_5$-$C_{30}$ carbocyclic group" as used herein refers to a monocyclic group or a polycyclic group, and, according to its chemical structure, may be a monovalent, divalent, trivalent, tetravalent, pentavalent, or hexavalent group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The term "$C_1$-$C_{30}$ heterocyclic group" as used herein refers to a monocyclic group or a polycyclic group, and, according to its chemical structure, may be a monovalent, divalent, trivalent, tetravalent, pentavalent, or hexavalent group.

At least one substituent of the substituted $C_5$-$C_{30}$ carbocyclic group, the substituted $C_1$-$C_{30}$ heterocyclic group, the substituted $C_1$-$C_{60}$ alkyl group, the substituted $C_1$-$C_{60}$ alkoxy group, the substituted $C_6$-$C_{60}$ aryl group, the substituted $C_7$-$C_{30}$ alkylaryl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{30}$ alkylheteroaryl group, the substituted $C_1$-$C_{30}$ heteroaryloxy group, the substituted $C_1$-$C_{30}$ heteroarylthio group, the substituted monovalent non-aromatic condensed polycyclic group, and the substituted monovalent non-aromatic condensed heteropolycyclic group may be selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), and Q$_1$ to Q$_9$, Q$_{11}$ to Q$_{19}$, Q$_{21}$ to Q$_{29}$, and Q$_{31}$ to Q$_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Others

The expression "A to B" as used herein refers to a range from A to B, including A and B.

While the embodiments of the present disclosure have been described with reference to the accompanying drawings, it is understood that the present disclosure is not limited to these embodiments. It is apparent to those of ordinary skill in the art that various modifications or changes may be made thereto without departing from the spirit and scope of the appended claims. It is understood that various modifications or changes fall within the technical scope of the present disclosure.

Hereinafter, a condensed cyclic compound represented by Formula 1 and an organic light-emitting device including the same will be described in detail with reference to Examples and Comparative Examples. Examples provided below are merely an example, and the condensed cyclic compound and the organic light-emitting device, according to embodiments, are not limited to Examples provided below.

The expression "B was used instead of A" used in describing Synthesis Examples means that a molar equivalent of "A" was identical to a molar equivalent of "B".
In addition, "%" is percent by weight (weight %) unless specified otherwise.
EXAMPLES
Synthesis Example 1: Synthesis of Compound 1
Compound 1 was synthesized according to the Reaction Scheme:
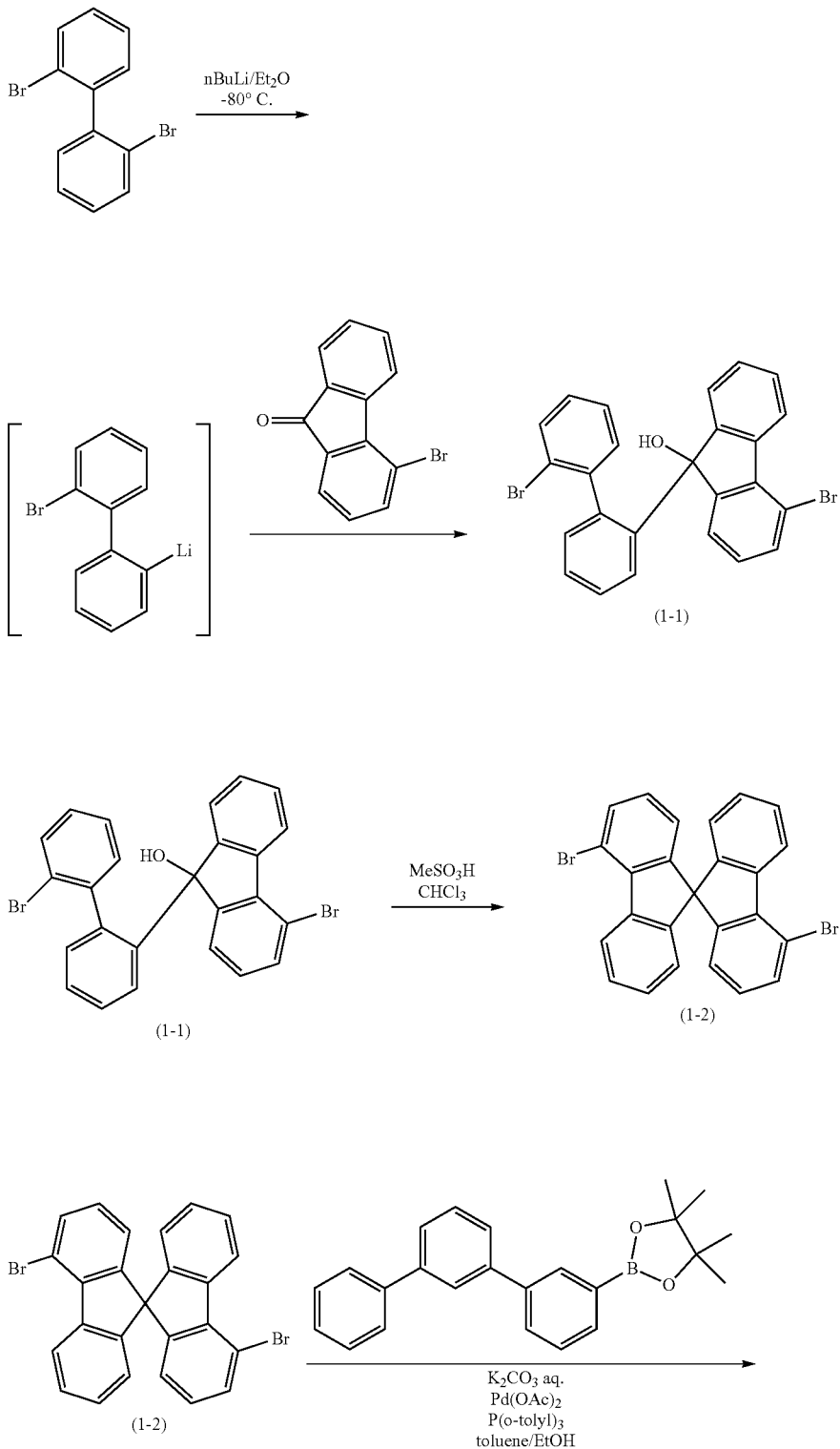

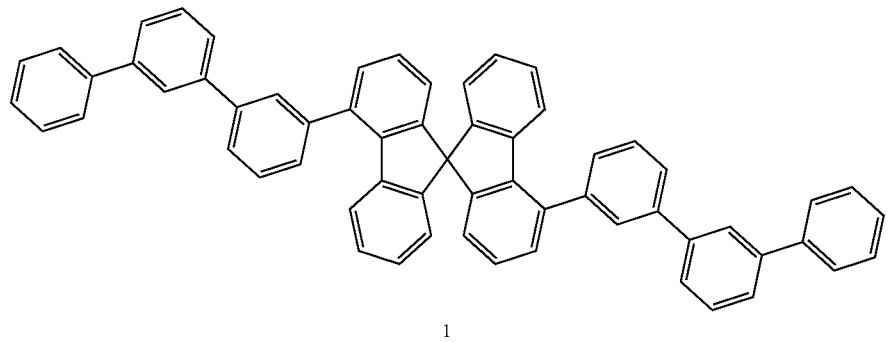

1

(1) Synthesis of Intermediate 1-1

In a nitrogen atmosphere, 2,2'-dibromo-1,1'-biphenyl (31.7 grams (g), 101.6 millimoles, mmol) and diethyl ether (500 milliliters, mL) were added to a three-neck flask and cooled to a temperature of −80° C. n-BuLi (34.7 mL of 2.66 molar (M) hexane solution, 92.4 mmol) was added dropwise thereto for 10 minutes. The mixture was stirred at a temperature of −80° C. for 5 minutes. Then, 4-bromo-9H-fluorene-9-one (25.0 g, 97 mmol) was added thereto and stirred at a temperature of −80° C. for 5 minutes. The mixture was heated to room temperature for 30 minutes and stirred at room temperature for 3 hours. The mixture was quenched with a small amount of water, and diluted with chloroform (500 mL), and washed with pure water twice. The organic layer obtained therefrom was dried by using anhydrous magnesium sulfate and filtered and concentrated by using a silica gel pad to obtain Intermediate 1-1, which was used to synthesize Intermediate 1-2 without purification.

(2) Synthesis of Intermediate 1-2

In a nitrogen atmosphere, Intermediate 1-1 and chloroform (500 mL) were added to a three-neck flask, and methane sulfonic acid (6.0 mL, 92.4 mmol) was added to the three-neck flask at room temperature. Then, the mixture was stirred at a temperature of 60° C. for 3 hours. The mixture was cooled to room temperature and washed with pure water twice. The organic layer obtained therefrom was dried by using anhydrous magnesium sulfate and filtered and concentrated by using a silica gel pad to obtain a crude product. The crude product was purified by silica gel chromatography (developing solvent hexane:chloroform=9:1) and recrystallized by using hexane to obtain Intermediate 1-2 (10.7 g, yield: 24%).

(3) Synthesis of Compound 1

In a nitrogen atmosphere, Intermediate 1-2 (7.1 g, 15 mmol), 2-([1,1',3'1''-terphenyl]-3-yl)-4,4,5,5-tetramethyl-1,3,2-dioxaborolane (12.8 g, 36 mmol), toluene (150 mL), ethanol (30 mL), and aqueous solution of 2 M potassium carbonate (60 mmol, 30 mL) were mixed at a three-neck flask, and tri(o-tolyl)phosphine (1.2 mmol) and palladium acetate (0.87 g, 0.75 mmol) were added thereto and stirred at a temperature of 80° C. for 8 hours. 500 mL of toluene was added thereto to dilute the mixture. The mixture was cooled to room temperature, washed with pure water twice, dried by using anhydrous magnesium sulfate, and filtered and concentrated by using a silica gel pad. The mixture was purified by silica gel chromatography (developing solvent hexane:toluene=8:2) and recrystallized by using hexane to obtain Compound 1 (6.96 g, yield: 60%).

Synthesis Example 2: Synthesis of Compound 3

Compound 3 was synthesized according to the Reaction Scheme:

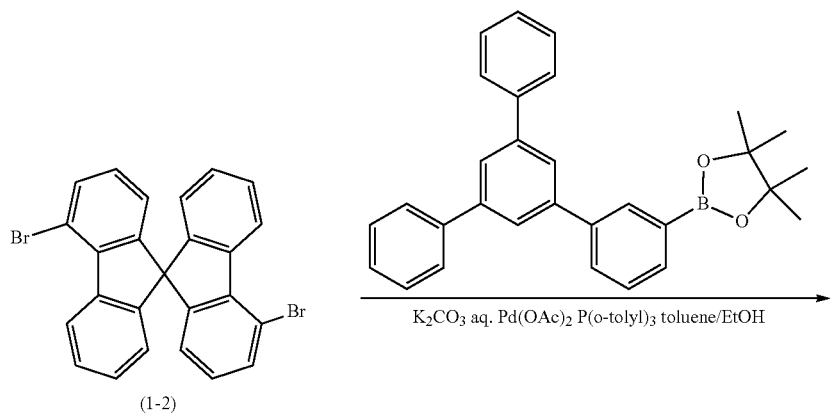

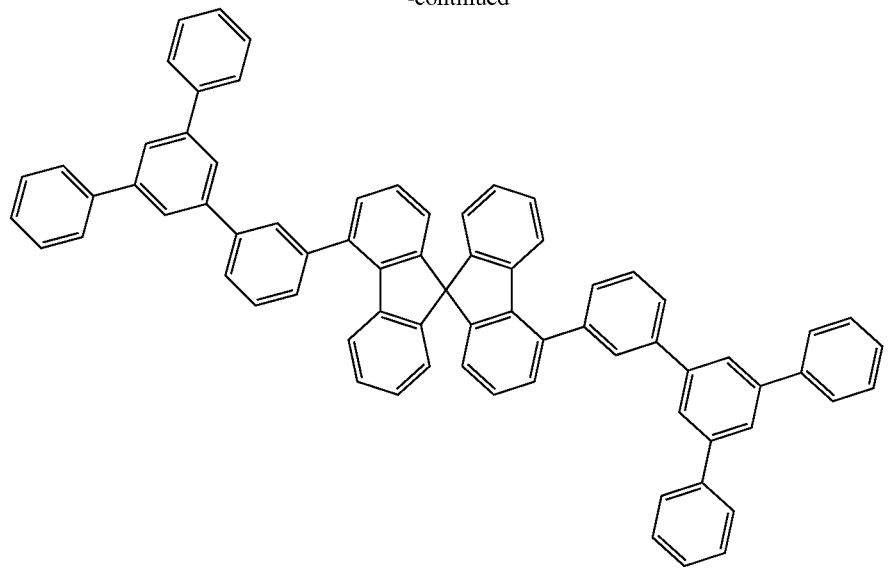

3

Compound 3 (7.63 g, yield: 55%) was obtained in the same manner as in Synthesis of Compound 1, except that 2-([1,1',3',1''-terphenyl]-3-yl)-4,4,5,5-tetramethyl-1,3,2-dioxaborolane was changed to 4,4,5,5-tetramethyl-2-(5'-phenyl-[1,1',3',1''-terphenyl]-3-yl)-1,3,2-dioxaborolane.

Evaluation Example 1: Measurement of Triplet Energy Level

Compound 1 was dissolved in toluene to a concentration of 3 weight % to prepare a solution. The same applied to Compounds 3 and C1 to prepare solutions. The solutions were spin-coated at a rotational speed of 1,600 revolutions per minute (rpm) and dried on a hot plate at a temperature of 120° C. for 15 minutes to obtain films (samples) having a thickness (film thickness after dry) of about 50 nanometers (nm). The samples were cooled to a temperature of 77 Kelvins (K) (−196° C.) and photoluminescence (PL) spectrums were obtained. The triplet energy levels (electron volts, eV) were calculated at the peak values of the shortest wavelengths of the PL spectrums. Results thereof are shown in Table 1.

TABLE 1

| | Triplet energy level (eV) |
|---|---|
| Compound 1 | 2.96 |
| Compound 3 | 2.96 |
| Compound C1 | 2.81 |
| Compound C2 | 2.91 |

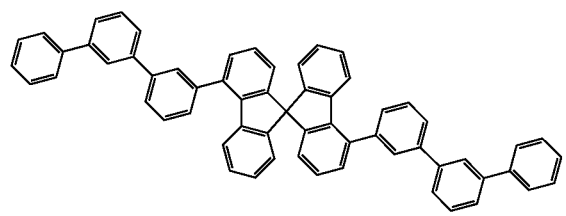

1

TABLE 1-continued

| | Triplet energy level (eV) |
|---|---|

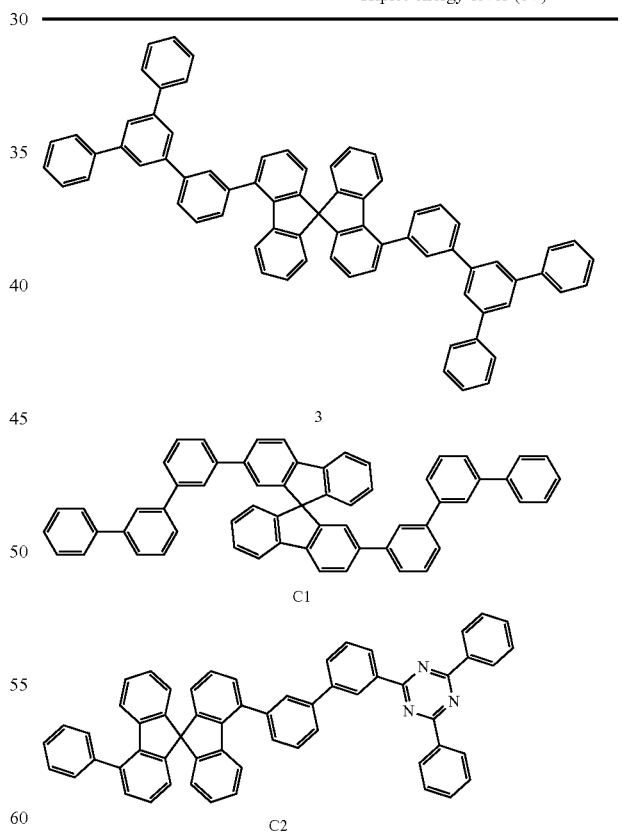

3

C1

C2

Referring to Table 1, it is confirmed that Compounds 1 and 3 have high triplet energy levels, as compared with Compounds C1 and C2, and thus are suitable for trapping triplet excitons. Therefore, it may be expected that an organic light-emitting device including Compound 1 or 3 will have high luminescent efficiency, as compared with an organic light-emitting device including Compound C1 or C2.

Evaluation Example 2: Measurement of Solubility 50 milligrams (mg) of Compound 1 and 500 mg of methyl benzoate (solvent) were added to a colorless sample bottle, ultrasonic waves were irradiated thereon at room temperature for 5 minutes, and the presence or absence of Compound 1 was visually confirmed. At this time, when Compound 1 does not remain, the solubility of Compound 1 is 10 weight % or more. When Compound 1 remains, a small amount of a solvent was added thereto, the irradiation of ultrasonic waves was repeated, and an amount of the solvent was measured until Compound 1 was completely dissolved. The solubility was measured from the amount of the solvent finally used. The solubility values of Compounds 3 and C1 were calculated in the same manner. Results thereof are shown in Table 2.

TABLE 2

|  | Solubility (weight %) |
| --- | --- |
| Compound 1 | 7 |
| Compound 3 | 9 |
| Compound C1 | 2 |
| Compound C2 | <1 |

Referring to Table 2, it is confirmed that Compounds 1 and 3 have high solubility to an organic solvent, as compared with Compounds C1 and C2. Therefore, it is confirmed that Compounds 1 and 3 are suitable for manufacturing an organic light-emitting device at low cost, as compared with Compounds C1 and C2.

Example 1

Poly(3,4-ethylene dioxythiophene)/poly(4-styrenesulfonate) (PEDOT/PSS) (manufactured by Sigma-Aldrich) were spin-coated on a glass substrate having a stripe-shaped 150-nm ITO (anode) to form a hole injection layer having a thickness (thickness of a dried film) of 30 nm.

Then, 1 weight % solution in which poly(9,9-dioctylfluorene-co-N-(4-butylphenyl)-diphenylamine) (TFB) was dissolved in xylene was spin-coated on the hole injection layer to form a hole transport layer having a thickness (thickness of a dried film) of 30 nm.

Then, a methyl benzoate solution containing Compound 1, H1 (hole transport host), E1 (electron transport host), and tris(2-(3-p-xylyl)phenyl)pyridine iridium (TEG) was spin-coated on the hole transport layer to form an emission layer having a thickness (thickness of a dried film) of 30 nm. At this time, Compound 1, H1, E1, and TEG were respectively 50 weight %, 40 weight %, 5 weight %, and 5 weight % based on the total weight of the emission layer.

Then, the resultant substrate including the emission layer was introduced into a vacuum evaporator, and 11-(4,6-diphenyl-1,3,5-triazine-2-yl)-12-phenyl-11,12-dihydroindolo[2,3-a]carbazole (HB1) was deposited on the emission layer to form a hole blocking layer having a thickness of 10 nm.

LiQ and KLET-03 were co-deposited on the hole blocking layer to form an electron transport layer having a thickness of 30 nm.

Then, aluminum was deposited on the electron transport layer to form a cathode having a thickness of 100 nm, thereby completing the manufacture of an organic light-emitting device.

The organic light-emitting device was sealed by using a glass encapsulation pipe including a drying agent and an ultraviolet curable resin in a globe box in which concentrations of moisture and oxygen were respectively 1 part per million (ppm) or less, and then used for evaluation.

TFB is a polymer compound having the following constitutional formula:

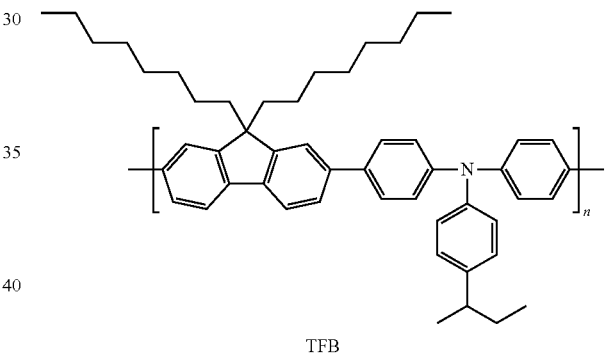

TFB

TFB has a weight average molecular weight (Mw)=320,000, a number average molecular weight (Mn)=98,000, and has PDI=3.3.

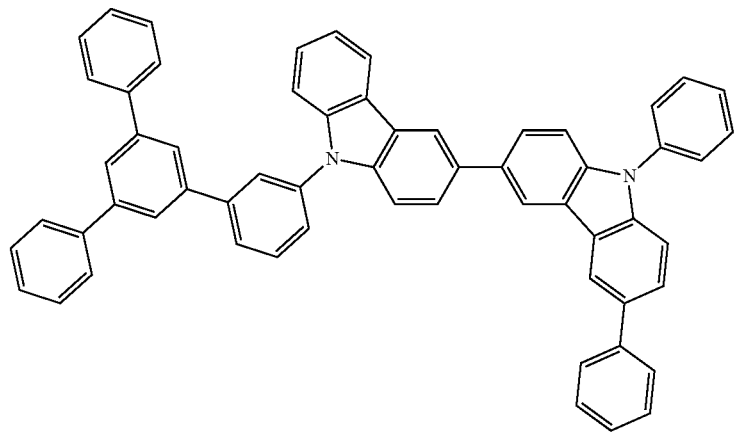

H1

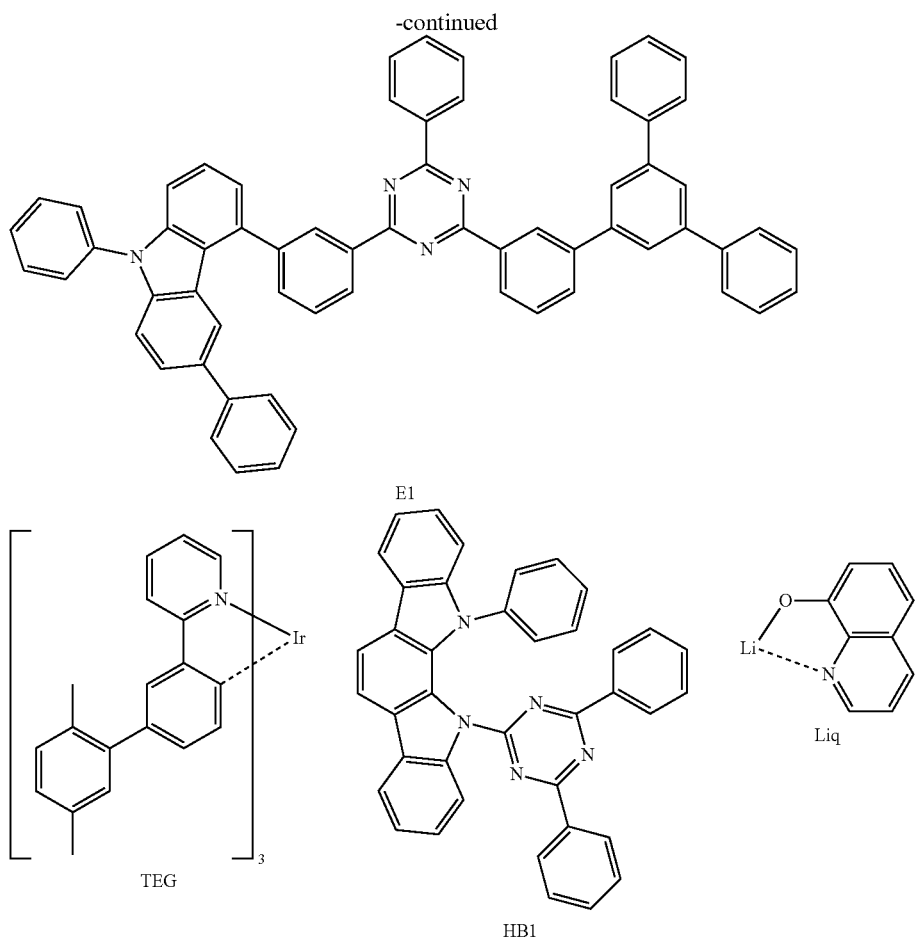

Example 2 and Comparative Examples 1 to 6

Organic light-emitting devices were manufactured in the same manner as in Example 1, except that an emission layer was changed to compositions shown in Table 3.

Evaluation Example 3

The current efficiency and light-emitting lifespan of the organic light-emitting devices of Examples 1 and 2 and Comparative Examples 1 to 6 were evaluated by using the following method. The organic light-emitting device was caused to emit light by applying a predetermined voltage thereto by using a DC constant voltage power supply (for example, Source Meter manufactured by KEYENCE). The light emission of the organic light-emitting device was measured by using a luminance measurement device (for example, SR-3 manufactured by Topcom), a current was set to be constant when a luminance was 6,000 candelas per square meter ($cd/m^2$) while gradually increasing a current applied thereto, and the organic light-emitting device was left.

Here, the current density (current value per unit area) of the organic light-emitting device was calculated, and the "current efficiency (candelas per ampere, cd/A)" was calculated by dividing the luminance ($cd/m^2$) by the current density (amperes per square meter, $A/m^2$).

In addition, the "light-emitting lifespan ($LT_{80}$, hours, hr)" indicates an amount of time until the luminance value measured by using the luminance measurement device gradually decreased and became 80% of initial luminance.

These evaluation results are shown in Table 3.

The current efficiency and light-emitting lifespan of Examples 1 and 2 and Comparative Examples 1 to 6 are relative values when the measured value of Comparative Example 1 is 100.

TABLE 3

|  | Material for emission layer (weight %) | Current efficiency | Light-emitting lifespan |
|---|---|---|---|
| Example 1 | Compound 1:H1:E1:TEG(50:40:5:5) | 125 | 113 |
| Example 2 | Compound 3:H1:E1:TEG(50:40:5:5) | 129 | 109 |
| Comparative Example 1 | Compound C1:H1:E1:TEG(50:40:5:5) | 100 | 100 |
| Comparative Example 2 | Compound C2:H1:E1:TEG(50:40:5:5) | 68 | 34 |
| Comparative Example 3 | H1:E1:TEG(90:5:5) | 114 | 118 |
| Comparative Example 4 | H1:E1:TEG(80:15:5) | 77 | 72 |
| Comparative Example 5 | H1:E1:TEG(70:25:5) | 56 | 24 |
| Comparative Example 6 | H1:E1:TEG(60:35:5) | 37 | 15 |

Referring to Table 3, it is confirmed that Examples 1 and 2 have improved current efficiency and lifespan, as compared with Comparative Examples 1 to 6.

In addition, Examples 1 and 2 do not include the condensed cyclic compound represented by Formula 1, and exhibit the lifespan substantially equal to that of Comparative Example 3 in which the carrier balance in the emission layer is optimized and more improved current efficiency than that of Comparative Example 3. Therefore, it is confirmed that it is possible to manufacture the organic light-emitting device including the condensed cyclic compound, which has improved luminescent efficiency and lifespan, by using solution process.

Since the condensed cyclic compound has improved electric characteristics and/or thermal stability, the organic light-emitting device including the condensed cyclic compound has improved current efficiency and lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present description as defined by the following claims.

What is claimed is:

1. A condensed cyclic compound represented by Formula 1:

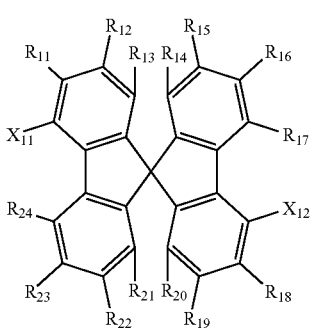

Formula 1

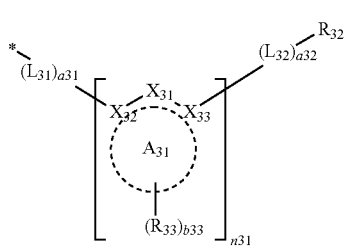

Formula 3

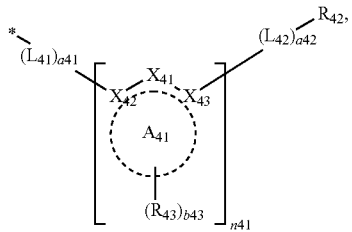

Formula 4 wherein, in Formulae 1, 3, and 4, $X_{11}$ is a group represented by Formula 3, and $X_{12}$ is a group represented by Formula 4, $X_{31}$ is selected from N and $C(R_{31})$, and $X_{41}$ is selected from N and $C(R_{41})$, $X_{32}$, $X_{33}$, $X_{42}$, and $X_{43}$ are each C, $A_{31}$ and $A_{41}$ are each independently selected from a $C_6$-$C_{60}$ arene group and a $C_1$-$C_{60}$ heteroarene group, $n_{31}$ and $n_{41}$ are each independently selected from 1, 2, 3, 4, 5, 6, 7, 8, 9, and 10, at least one of $n_{31}$ and $n_{41}$ is selected from 2, 3, 4, 5, 6, 7, 8, 9, and 10, $L_{31}$, $L_{32}$, $L_{41}$, and $L_{42}$ are each independently selected from a single bond, a substituted or unsubstituted $C_5$-$C_{60}$ carbocyclic group, and a substituted or unsubstituted $C_1$-$C_{60}$ heterocyclic group, a31, a32, a41, and a42 are each independently selected from 0, 1, 2, and 3, $R_{32}$ and $R_{42}$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{11}$ to $R_{24}$, $R_{31}$, $R_{33}$, $R_{41}$, and $R_{43}$ are each independently selected from hydrogen, deuterium, —F, —Cl, —Br, —I, a cyano group, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —N($Q_1$)($Q_2$), b33 and b43 are each independently selected from 1, 2, 3, 4, 5, 6, 7, 8, 9, and 10, Q1 to Q3 are each independently selected from hydrogen, deuterium, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a $C_1$-$C_{60}$ alkyl group substituted with at least one selected from deuterium, —F, a cyano group, a $C_1$-$C_{60}$ alkyl group, and a $C_6$-$C_{60}$ aryl group, and a $C_6$-$C_{60}$ aryl group substituted with at least one selected from deuterium, —F, a cyano group, a $C_1$-$C_{60}$ alkyl group, and a $C_6$-$C_{60}$ aryl group, and

* indicates a binding site to a neighboring atom.

2. The condensed cyclic compound of claim 1, wherein $A_{31}$ and $A_{41}$ are each independently selected from a benzene group, a naphthalene group, a pyridine group, a pyridazine group, a pyrimidine group, a pyrazine group, a triazine group, a quinoline group, an isoquinoline group, a quinazoline group, a quinoxaline group, and a naphthyridine group.

3. The condensed cyclic compound of claim 1, wherein $n_{31}$ and $n_{41}$ are each independently selected from 1, 2, and 3.

4. The condensed cyclic compound of claim 1, wherein $L_{31}$, $L_{32}$, $L_{41}$, and $L_{42}$ are each independently selected from:

a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthalene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiophene group, a silole group, a benzofuran group, a benzothiophene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazolinone group, a benzimidazolinone group, an imidazopyridine group, an imidazopyrimidine group, an imidazophenanthridine group, a benzimidazophenanthridine group, an azadibenzofuran group, an azacarbazole group, an azadibenzothiophene group, a diazadibenzofuran group, a diazacarbazole group, a diazadibenzothiophene group, a xanthone group, and a thioxanthone group; and a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthalene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiophene group, a silole group, a benzofuran group, a benzothiophene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazolinone group, a benzimidazolinone group, an imidazopyridine group, an imidazopyrimidine group, an imidazophenanthridine group, a benzimidazophenanthridine group, an azadibenzofuran group, an azacarbazole group, an azadibenzothiophene group, a diazadibenzofuran group, a diazacarbazole group, a diazadibenzothiophene group, a xanthone group, and a thioxanthone group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group.

5. The condensed cyclic compound of claim 1, wherein $R_{32}$ and $R_{42}$ are each independently selected from:

a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group; and a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a coumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazcarbazolyl group, a diazadibenzothienyl group, a xanthonyl group, and a thioxanthonyl group.

6. The condensed cyclic compound of claim 1, wherein $R_{32}$ and $R_{42}$ are each independently selected from:

a phenyl group, a naphthyl group, a fluorenyl group, a phenanthrenyl group, a biphenyl group, a terphenyl group, a triphenylenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, a carbazolyl group, an imidazolyl group, and a benzimidazolyl group; and a phenyl group, a naphthyl group, a fluorenyl group, a phenanthrenyl group, a biphenyl group, a terphenyl group, a triphenylenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, a carbazolyl group, an imidazolyl group, and a benzimidazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{30}$ alkyl group, a $C_1$-$C_{30}$ alkoxy group, a phenyl group, a naphthyl group, a biphenyl group, and a terphenyl group.

7. The condensed cyclic compound of claim 1, wherein $R_{11}$ to $R_{24}$, $R_{31}$, $R_{33}$, $R_{41}$, and $R_{43}$ are each independently selected from hydrogen, deuterium, —F, —Cl, —Br, —I, a cyano group, a $C_1$-$C_{30}$ alkyl group, a $C_1$-$C_{30}$ alkoxy group, a $C_6$-$C_{30}$ aryl group, a $C_6$-$C_{30}$ aryloxy group, a $C_1$-$C_{30}$ heteroaryl group, a $C_1$-$C_{30}$ heteroaryloxy group, a monovalent non-aromatic condensed polycyclic group, a substituted or unsubstituted monovalent non-aromatic condensed heteropolycyclic group, and —N($Q_1$)($Q_2$), and $Q_1$ and $Q_2$ are each independently a $C_1$-$C_{30}$ alkyl group.

8. The condensed cyclic compound of claim 1, wherein $X_{11}$ is selected from groups represented by Formulae 3-2 to 3-3, and $X_{12}$ is selected from groups represented by Formulae 4-2 to 4-3:

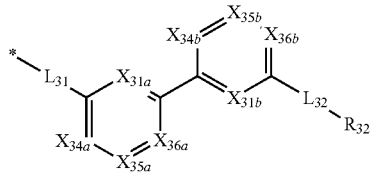

3-2

3-3

4-2

4-3 wherein, in Formulae 3-2 to 3-3 and 4-2 to 4-3, $L_{31}$, $L_{32}$, and $R_{32}$ are each independently the same as described in Formula 3, $L_{41}$, $L_{42}$, and $R_{42}$ are each independently the same as described in Formula 4, $X_{31a}$ to $X_{31c}$ are each independently the same as described in connection with $X_{31}$ in Formula 3, $X_{41a}$ to $X_{41c}$ are each independently the same as described in connection with $X_{41}$ in Formula 4, $X_{34a}$ is selected from N and C($R_{34a}$), $X_{34b}$ is selected from N and C($R_{34b}$), and $X_{34c}$ is selected from N and C($R_{34c}$), $X_{35a}$ is selected from N and C($R_{35a}$), $X_{35b}$ is selected from N and C($R_{35b}$), and $X_{35c}$ is selected from N and C($R_{35c}$), $X_{36a}$ is selected from N and C($R_{36a}$), $X_{36b}$ is selected from N and C($R_{36b}$), and $X_{36c}$ is selected from N and C($R_{36c}$), $X_{44a}$ is selected from N and C($R_{44a}$), $X_{44b}$ is selected from N and C($R_{44b}$), and $X_{44c}$ is selected from N and C($R_{34c}$), $X_{45a}$ is selected from N and C($R_{45a}$), $X_{45b}$ is selected from N and C($R_{45b}$), and $X_{45c}$ is selected from N and C($R_{45c}$), $X_{46a}$ is selected from N and C($R_{46a}$), $X_{46b}$ is selected from N and C($R_{46b}$), and $X_{46c}$ is selected from N and C($R_{46c}$), $R_{34a}$ to $R_{34c}$, $R_{35a}$ to $R_{35c}$, and $R_{36a}$ to $R_{36c}$ are each independently the same as described in connection with $R_{33}$ in Formula 3, $R_{44a}$ to $R_{44c}$, $R_{45a}$ to $R_{45c}$, and $R_{46a}$ to $R_{46c}$ are each independently the same as described in connection with $R_{43}$ in Formula 4, and

* indicates a binding site to a neighboring atom.

9. The condensed cyclic compound of claim 8, wherein $X_{11}$ is a group represented by Formula 3-2, and $X_{12}$ is a group represented by Formula 4-2; or $X_{11}$ is a group represented by Formula 3-3, and $X_{12}$ is a group represented by Formula 4-3.

10. The condensed cyclic compound of claim 1, wherein the condensed cyclic compound is represented by one selected from Formulae 1-1 and 1-2:

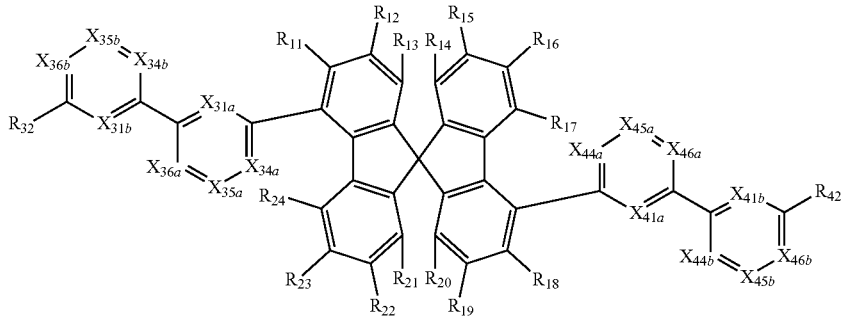

1-1

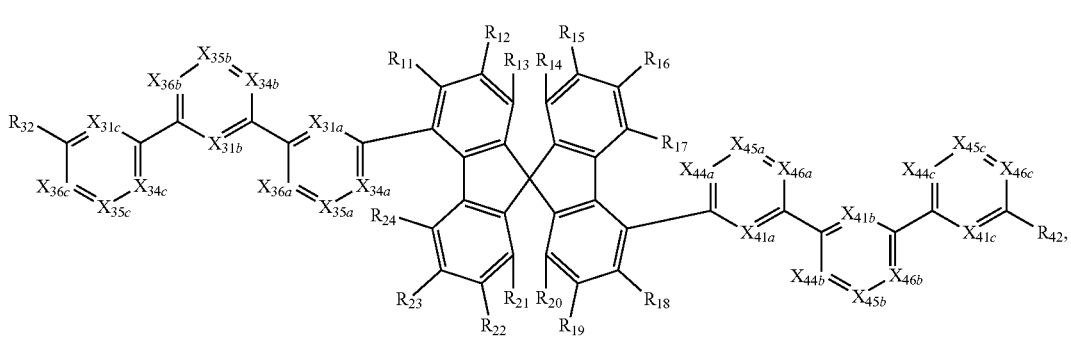

1-2 wherein, in Formulae 1-1 and 1-2, $R_{11}$ to $R_{24}$, $R_{32}$, and $R_{42}$ are each independently the same as described in Formula 1, $X_{31a}$ to $X_{31c}$ are each independently the same as described in connection with $X_{31}$ in Formula 3, $X_{41a}$ to $X_{41c}$ are each independently the same as described in connection with $X_{41}$ in Formula 4, $X_{34a}$ is selected from N and $C(R_{34a})$, $X_{34b}$ is selected from N and $C(R_{34b})$, and $X_{34c}$ is selected from N and $C(R_{34c})$, $X_{35a}$ is selected from N and $C(R_{35a})$, $X_{35b}$ is selected from N and $C(R_{35b})$, and $X_{35c}$ is selected from N and $C(R_{35c})$, $X_{36a}$ is selected from N and $C(R_{36a})$, $X_{36b}$ is selected from N and $C(R_{36b})$, and $X_{36c}$ is selected from N and $C(R_{36c})$, $X_{44a}$ is selected from N and $C(R_{44a})$, $X_{44b}$ is selected from N and $C(R_{44b})$, and $X_{44c}$ is selected from N and $C(R_{34c})$, $X_{45a}$ is selected from N and $C(R_{45a})$, $X_{45b}$ is selected from N and $C(R_{45b})$, and $X_{45c}$ is selected from N and $C(R_{45c})$, $X_{46a}$ is selected from N and $C(R_{46a})$, $X_{46b}$ is selected from N and $C(R_{46b})$, and $X_{46c}$ is selected from N and $C(R_{46c})$, $R_{34a}$ to $R_{34c}$, $R_{35a}$ to $R_{35c}$, and $R_{36a}$ to $R_{36c}$ are each independently the same as described in connection with $R_{33}$ in Formula 3, and $R_{44a}$ to $R_{44c}$, $R_{45a}$ to $R_{45c}$, and $R_{46a}$ to $R_{46c}$ are each independently the same as described in connection with $R_{43}$ in Formula 4.

11. A condensed cyclic compound selected from Compounds 1 to 16:

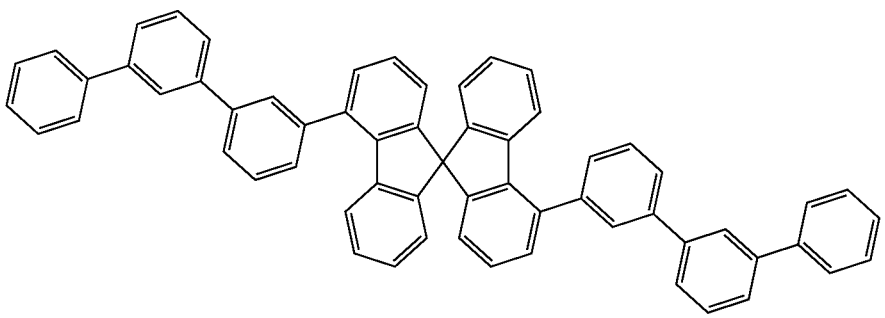

1

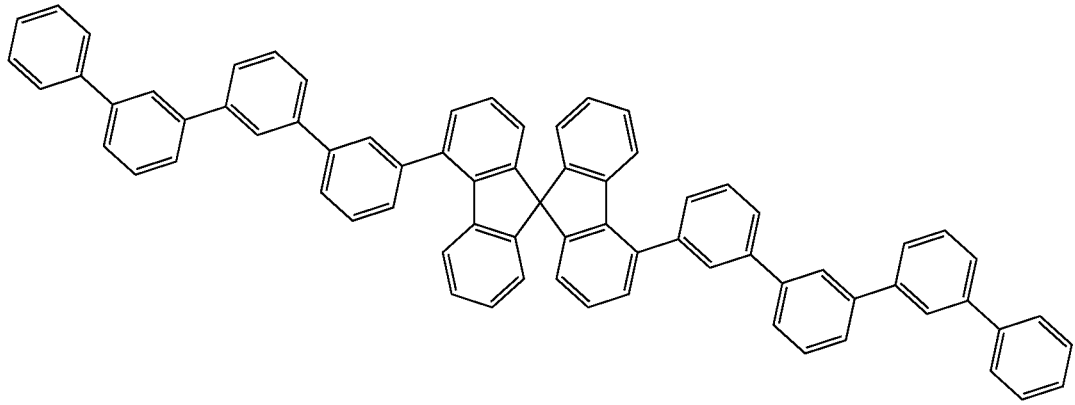
2
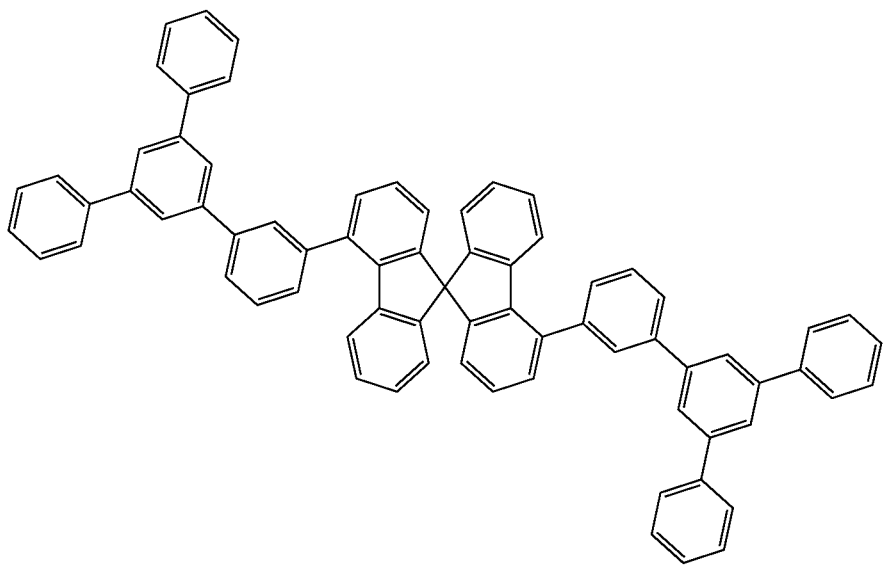
3
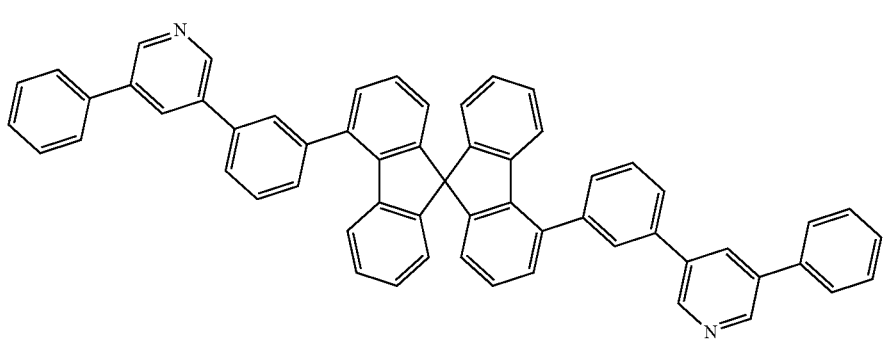
4
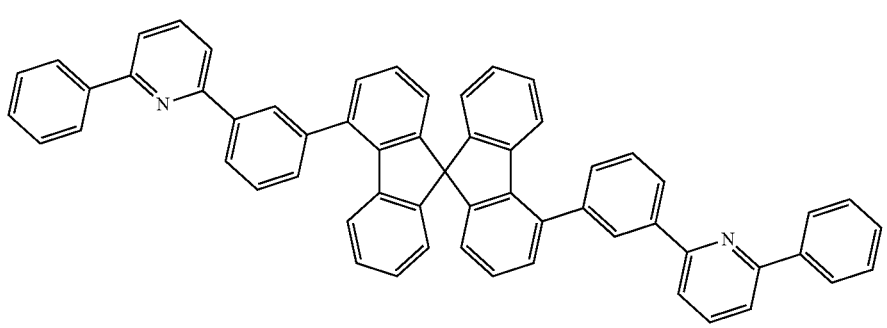
5

6
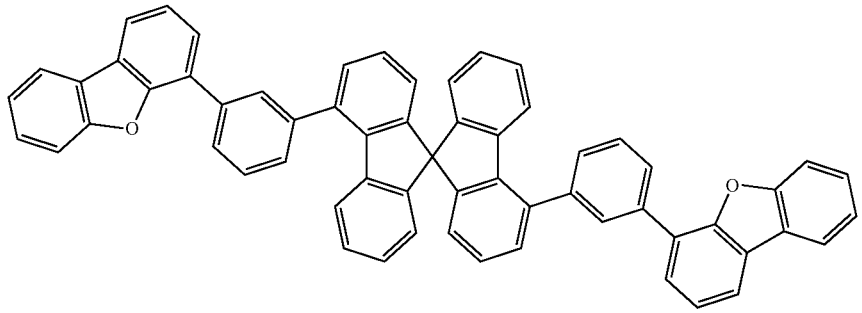
7
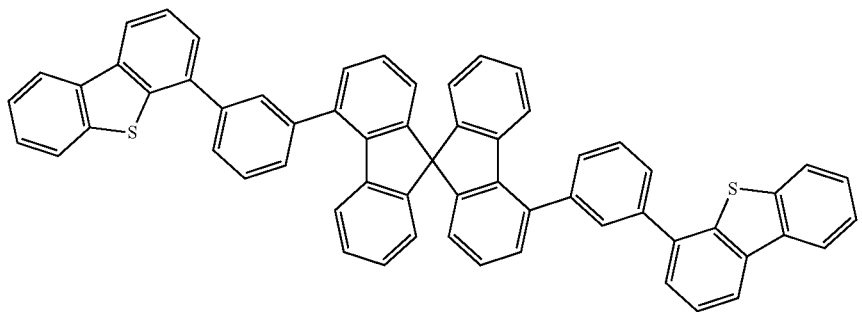
8
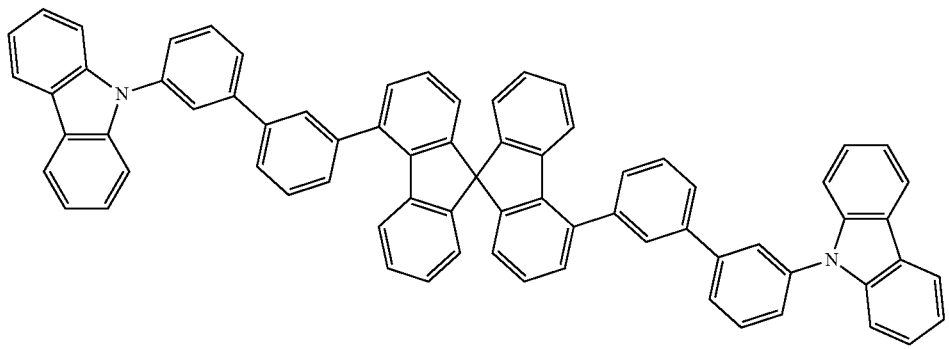
9
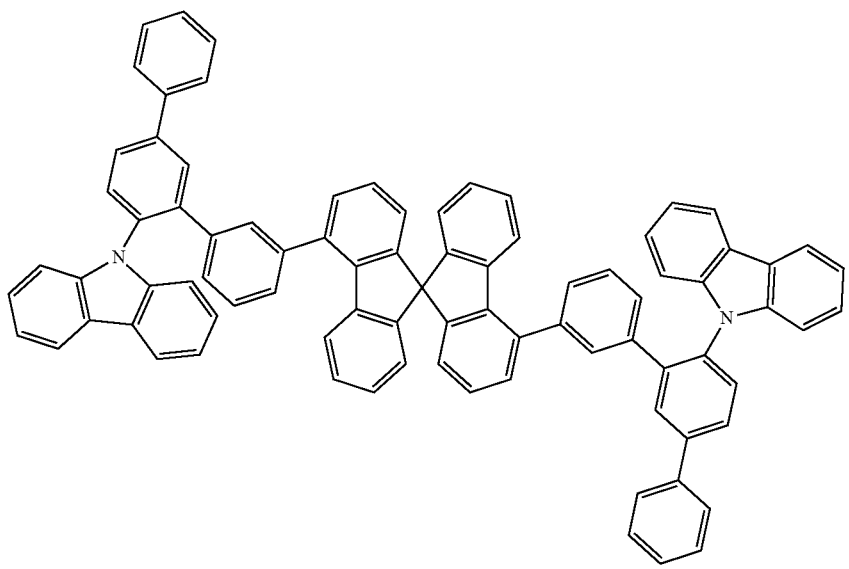

10
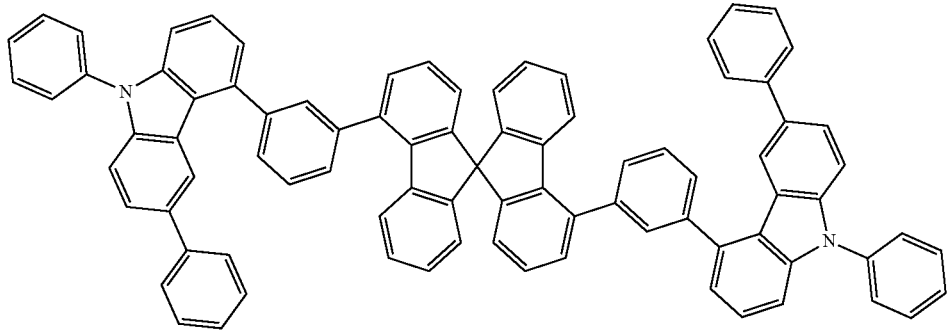
11
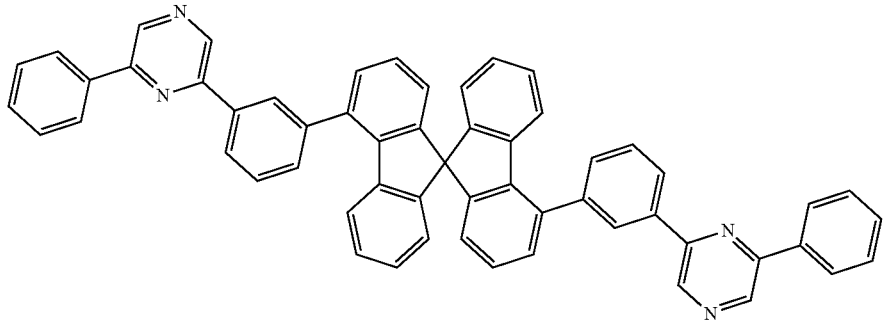
12
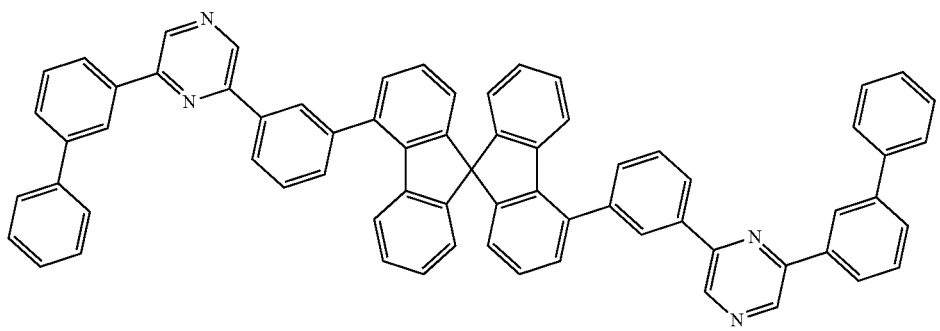
13
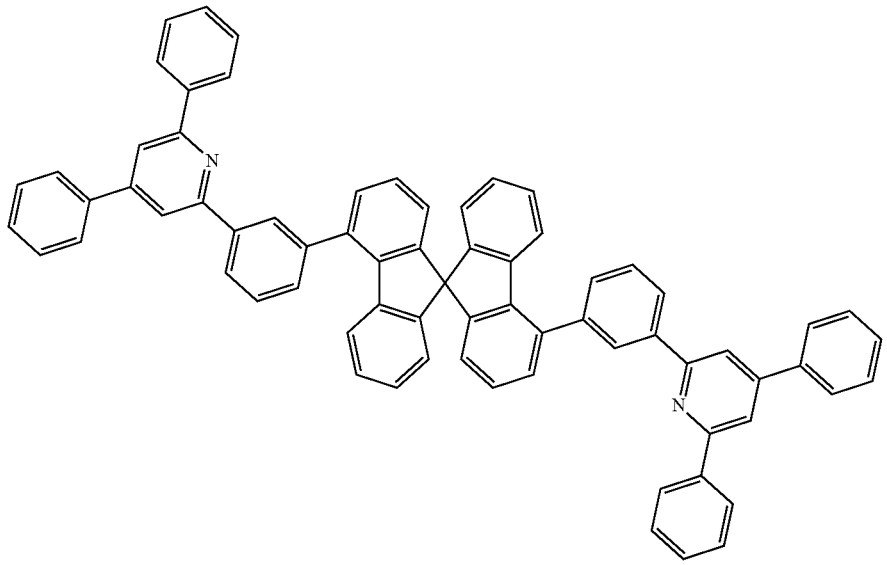

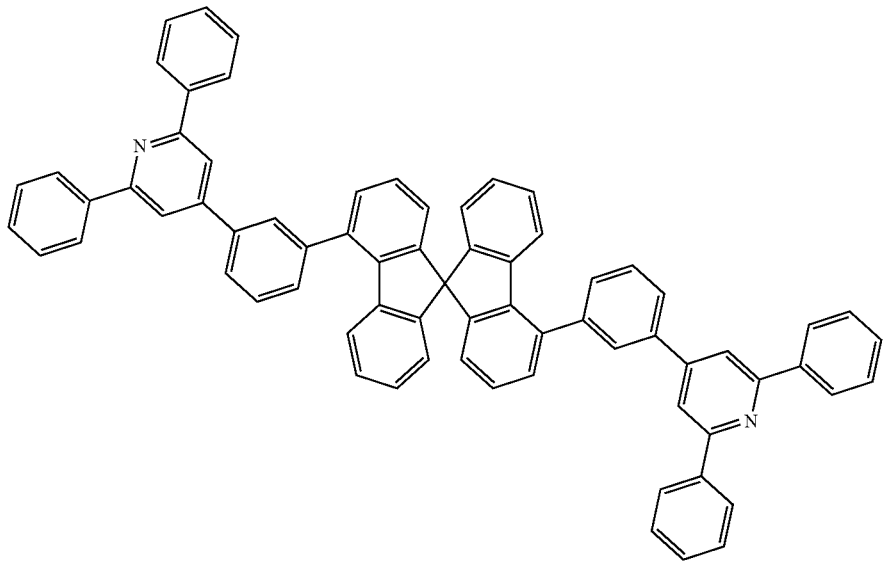
14
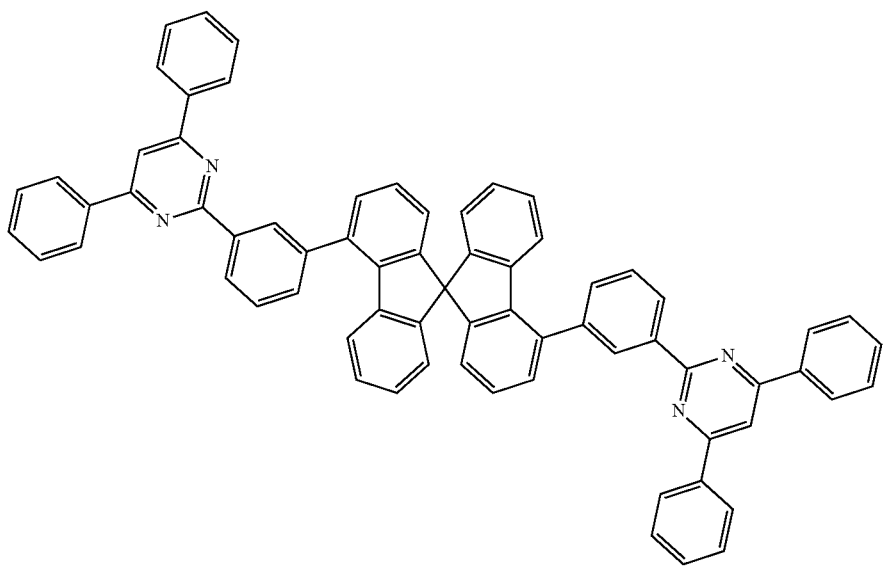
15

-continued

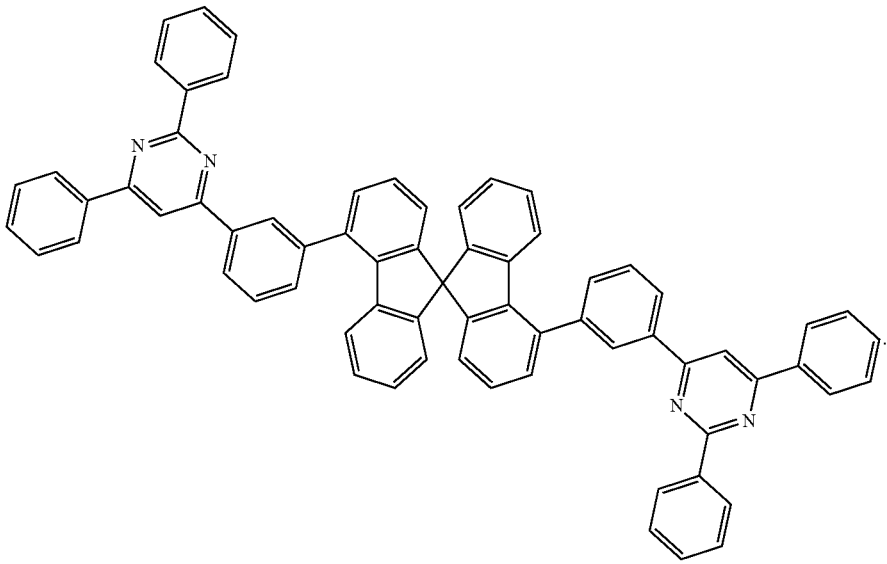

12. A composition comprising at least one of the condensed cyclic compound represented by Formula 1 of claim 1.

13. The composition of claim 12, further comprising at least one selected from a first compound represented by Formula 5 and a second compound represented by Formula 6:

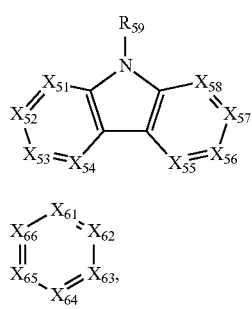

Formula 5

Formula 6 wherein, in Formulae 5 and 6, $X_{51}$ is N or $C(R_{51})$; $X_{52}$ is N or $C(R_{52})$; $X_{53}$ is N or $C(R_{53})$; $X_{54}$ is N or $C(R_{54})$; $X_{55}$ is N or $C(R_{55})$; $X_{56}$ is N or $C(R_{56})$; $X_{57}$ is N or $C(R_{57})$; and $X_{58}$ is N or $C(R_{58})$, $X_{61}$ is N or $C(R_{61})$; $X_{62}$ is N or $C(R_{62})$; $X_{63}$ is N or $C(R_{63})$; $X_{64}$ is N or $C(R_{64})$; $X_{65}$ is N or $C(R_{65})$; and $X_{66}$ is N or $C(R_{66})$, wherein at least one selected from $X_{61}$ to $X_{66}$ is N, $R_{51}$ to $R_{58}$ and $R_{61}$ to $R_{66}$ are each independently selected from hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{59}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $R_{61}$ to $R_{66}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

14. The composition of claim 13, comprising the first compound and the second compound.

15. The composition of claim 12, further comprising a light-emitting material.

16. The composition of claim 15, wherein
    the light-emitting material comprises an organometallic compound.

17. The composition of claim 12, further comprising a solvent.

18. An organic light-emitting device comprising:
    a first electrode;
    a second electrode; and
    an organic layer disposed between the first electrode and the second electrode and comprising an emission layer,
    wherein the organic layer comprises at least one of the condensed cyclic compound represented by Formula 1 of claim 1.

19. The organic light-emitting device of claim 18, wherein
    the organic layer further comprises a light-emitting material, and
    the light-emitting material emits light from triplet excitons.

* * * * *